(12) United States Patent
Kenny et al.

(10) Patent No.: US 11,045,578 B2
(45) Date of Patent: Jun. 29, 2021

(54) TISSUE ENGINEERING SCAFFOLDS COMPRISING PARTICULATE EGG SHELL MEMBRANE

(71) Applicant: BIOVOTEC AS, Oslo (NO)

(72) Inventors: Enda Kenny, Dublin (IE); Ralf Schmidt, Oslo (NO); Henri-Pierre Suso, Oslo (NO); Matthias Schnabelrauch, Jena (DE); Annika Wartenberg, Jena (DE)

(73) Assignee: BIOVOTEC AS, Oslo (NO)

( * ) Notice: Subject to any disclaimer, the term of this patent is extended or adjusted under 35 U.S.C. 154(b) by 464 days.

(21) Appl. No.: 15/738,962

(22) PCT Filed: Jun. 24, 2016

(86) PCT No.: PCT/EP2016/064674
§ 371 (c)(1),
(2) Date: Dec. 21, 2017

(87) PCT Pub. No.: WO2016/207355
PCT Pub. Date: Dec. 29, 2016

(65) Prior Publication Data
US 2020/0030492 A1    Jan. 30, 2020

Related U.S. Application Data

(63) Continuation of application No. PCT/EP2016/064674, filed on Jun. 24, 2016.

(30) Foreign Application Priority Data

Jun. 24, 2015 (GB) .................................. 1511146.1
Jul. 1, 2015 (GB) .................................. 1511579.3

(51) Int. Cl.
| | |
|---|---|
| A61L 27/36 | (2006.01) |
| A61L 27/38 | (2006.01) |
| A61L 27/44 | (2006.01) |
| A61L 27/54 | (2006.01) |
| A61L 27/56 | (2006.01) |
| A61P 17/02 | (2006.01) |
| A61L 27/58 | (2006.01) |

(52) U.S. Cl.
CPC ....... *A61L 27/3604* (2013.01); *A61L 27/3891* (2013.01); *A61L 27/44* (2013.01); *A61L 27/54* (2013.01); *A61L 27/56* (2013.01)

(58) Field of Classification Search
CPC ...... A61L 27/3604; A61L 27/56; A61L 27/54; A61L 27/44; A61L 27/58; A61L 27/3691; A61P 17/02
USPC ..................................................... 435/325
See application file for complete search history.

(56) References Cited

U.S. PATENT DOCUMENTS

| | | |
|---|---|---|
| 3,194,732 A | 7/1965 | Neuhauser et al. |
| 3,196,075 A | 7/1965 | Neuhauser |
| 3,400,199 A | 9/1968 | Balassa |
| 3,558,771 A | 1/1971 | Balassa et al. |
| 3,804,949 A | 4/1974 | Balassa |
| 5,356,614 A | 10/1994 | Sharma |
| 5,503,847 A | 4/1996 | Queen et al. |
| 6,201,164 B1 | 3/2001 | Wulff et al. |
| 6,541,447 B1 | 4/2003 | Dawson |
| 6,946,551 B2 | 9/2005 | Long et al. |
| 7,767,297 B2 | 8/2010 | Tajima et al. |
| 7,780,994 B2 | 8/2010 | Lynn et al. |
| 8,173,174 B2 | 5/2012 | Strohbehn et al. |
| 8,197,852 B2 | 6/2012 | Strohbehn et al. |
| 8,197,853 B2 | 6/2012 | Strohbehn et al. |
| 8,211,477 B2 | 7/2012 | Strohbehn et al. |
| 8,425,943 B2 | 4/2013 | Strohbehn et al. |
| 8,580,315 B2 | 11/2013 | Devore et al. |
| 2004/0180025 A1 | 9/2004 | Long et al. |
| 2004/0180851 A1 | 9/2004 | Long et al. |
| 2005/0107302 A1 | 5/2005 | Dawson |
| 2005/0246840 A1 | 11/2005 | Sano et al. |
| 2006/0159816 A1 | 7/2006 | Vlad |
| 2007/0178170 A1 | 8/2007 | DeVore et al. |
| 2007/0225220 A1 | 9/2007 | Ming et al. |
| 2008/0063677 A1 * | 3/2008 | Long ..................... A61Q 19/08 424/401 |
| 2008/0124381 A1 | 5/2008 | Barnhart et al. |
| 2008/0146869 A1 | 6/2008 | Chow et al. |

(Continued)

FOREIGN PATENT DOCUMENTS

| | | |
|---|---|---|
| BE | 677335 A | 9/1966 |
| CA | 721555 A | 11/1965 |

(Continued)

OTHER PUBLICATIONS

Balaz, Matej; "Eggshell Membrane Biomaterial as a Platform for Applications in Materials Science"; Acta Biomaterialia; 10; pp. 3827-3843; (2014).

(Continued)

*Primary Examiner* — Kara D Johnson
(74) *Attorney, Agent, or Firm* — Cantor Colburn LLP

(57) ABSTRACT

The invention provides a three dimensional (3D), porous, biodegradable and biocompatible tissue engineering scaffold, wherein at least 25% w/w of the scaffold is particulate egg shell membrane (ESM) distributed substantially uniformly therein and the scaffold is essentially dry. Methods for preparing the same by freeze-drying and cryogelation and the use thereof in methods of tissue engineering and to promote the healing of wounds are also provided.

21 Claims, 2 Drawing Sheets

(56) References Cited

U.S. PATENT DOCUMENTS

| | | |
|---|---|---|
| 2009/0031691 A1 | 2/2009 | Tajima et al. |
| 2009/0074879 A1 | 3/2009 | Braguti |
| 2009/0104173 A1 | 4/2009 | Strohbehn et al. |
| 2009/0206009 A1 | 8/2009 | Floh et al. |
| 2010/0254961 A1* | 10/2010 | Nishio .................... A61K 8/64 424/94.1 |
| 2010/0266646 A1 | 10/2010 | Dvorak et al. |
| 2011/0150961 A1 | 6/2011 | Perry et al. |
| 2013/0035473 A1 | 2/2013 | Summers et al. |
| 2013/0337080 A1 | 12/2013 | Wedekind et al. |
| 2013/0344129 A1 | 12/2013 | Washburn et al. |
| 2014/0294961 A1 | 10/2014 | Kato et al. |
| 2014/0348939 A1 | 11/2014 | Blaine et al. |
| 2017/0319629 A1 | 11/2017 | Schmidt et al. |
| 2018/0032574 A1 | 11/2018 | Kenny et al. |

FOREIGN PATENT DOCUMENTS

| | | |
|---|---|---|
| CN | 1295848 A | 5/2001 |
| CN | 1432592 A | 7/2003 |
| CN | 1569244 A | 1/2005 |
| CN | 101288669 A | 10/2008 |
| CN | 101317965 A | 12/2008 |
| CN | 101439114 A | 5/2009 |
| CN | 101575771 A | 11/2009 |
| CN | 101697815 A | 4/2010 |
| CN | 101822783 A | 9/2010 |
| CN | 101837094 A | 9/2010 |
| CN | 102517363 A | 6/2012 |
| CN | 103275205 A | 9/2013 |
| CN | 103300357 A | 9/2013 |
| EP | 2020455 A2 | 2/2009 |
| FR | 1348353 A | 1/1964 |
| FR | 2035769 A1 | 12/1970 |
| GB | 949946 | 2/1964 |
| GB | 1251720 | 10/1971 |
| IN | 00315DE2006 A | 8/2007 |
| IN | 01957MU2008 | 3/2010 |
| JP | 63309273 A | 12/1988 |
| JP | 2231426 A | 9/1990 |
| JP | H02231426 A | 9/1990 |
| JP | 5015581 A | 1/1993 |
| JP | 6192443 A | 7/1994 |
| JP | 7138142 A | 5/1995 |
| JP | 7277949 A | 10/1995 |
| JP | 9241146 A | 9/1997 |
| JP | 11228438 A | 8/1999 |
| JP | 2002212069 A | 7/2002 |
| JP | 2002249440 A | 9/2002 |
| JP | 2002265350 A | 9/2002 |
| JP | 2003225298 A | 8/2003 |
| JP | 2003246741 A | 9/2003 |
| JP | 2004018471 A | 1/2004 |
| JP | 2005194401 A | 7/2005 |
| JP | 2006069892 A | 3/2006 |
| JP | 3814247 B2 | 8/2006 |
| JP | 2006326018 A | 12/2006 |
| JP | 2007197393 A | 8/2007 |
| JP | 2008007419 A | 1/2008 |
| JP | 4187976 A | 11/2008 |
| JP | 2009089858 A | 4/2009 |
| JP | 2013040115 A | 2/2013 |
| JP | 2013216652 A | 10/2013 |
| KR | 20130103406 A | 9/2013 |
| TR | 201006790 A2 | 12/2010 |
| WO | 9951175 A1 | 10/1999 |
| WO | 200170194 A1 | 9/2001 |
| WO | 2004080388 A2 | 9/2004 |
| WO | 2004080428 A2 | 9/2004 |
| WO | 2005023176 A2 | 3/2005 |
| WO | 2005039499 A2 | 5/2005 |
| WO | 2005040228 A2 | 5/2005 |
| WO | 2005107774 A1 | 11/2005 |
| WO | 2009048924 A1 | 4/2009 |
| WO | 2010006260 A1 | 1/2010 |
| WO | 2010086616 A1 | 8/2010 |
| WO | 2010122490 A2 | 10/2010 |
| WO | 2012036645 A2 | 3/2012 |
| WO | 2012112410 A2 | 8/2012 |
| WO | 2014028327 A1 | 2/2014 |
| WO | 2014190227 A1 | 11/2014 |
| WO | 2015009256 A1 | 1/2015 |
| WO | WO-2015009256 A1 * | 1/2015 ......... A61L 27/3683 |
| WO | 2015058790 A1 | 4/2015 |
| WO | 2016066718 A1 | 5/2016 |

OTHER PUBLICATIONS

Chen et al.; "Preparation and Characterization of Polyurethane/soluble Eggshell Membrane Nanofibers"; Bio-Medical Materials and Engineering; 24; pp. 1979-1989; (2014).

CN101317965 A English Abstract; Sep. 23, 2015; 1 page.

Eming et al.; "Inflammation in Wound Repair: Molecular and Cellular Mechanisms"; Journal of Investigative Dermatology; 127; pp. 514-525; (2007).

GB14191831 Search Report, dated Jun. 30, 2015 6 pages.

Hwang et al.; "Poly(ethylene glycol) Cryogels as Potential Cell Scaffolds: Effect of Polymerization Conditions on Cryogel Microstructure and Properties"; J. Mater. Chem.; 20; pp. 345-351; (2010).

International Search Report and Written Opinion: International Application No. PCT/EP2016/064674; International Filing Date Jun. 24, 2015; dated Sep. 26, 2016; 13 pages.

Johnson, et al.; "Randomized, Controlled Trial of Topical Exit-Site Application of Honey (Medihoney) versus Mupirocin for the Prevention of Catheter-Associated Infections in Hemodialysis Patients"; J AM Soc Nephrol; 16; pp. 1456-1462;(2005).

JPH02231426 A English Asbstract; 1 page; Sep. 23, 2015.

Loh et al.; "Three-Dimensional Scaffolds for Tissue Engineering Applications: Role of Porosity and Pore Size"; Tissue Engineering: Part B, 19(6); pp. 485-501; (2013).

Murphy et al.; "Understanding the Effect of Mean Pore Size on Cello Activity in Collagen-glycosaminoglycan Scaffolds"; Cell Adhesion & Migration; 4:3; pp. 377-381; (2010).

Ratanavaraporn et al.; "Effects of Acid Type on Physical and Biological Properties of Collagen Scaffolds"; J. Biomater. Sci. Polymer Edn., 19(7); pp. 945-952; (2008).

Yang et al.; "Egg Membrane as a New Biological Dressing in Split-Thickness Skin Graft Donor Sites: A Preliminary Clinical Evaluation"; Chang Gung Med J; 26(3); pp. 153-158; (2003).

Yannas et al.; "Synthesis and Characterization of a Model Extracellular Matrix that Induces Partial Regeneration of Adult Mammalian Skin"; Proc. Natl. Acad. Sci. USA; 86; pp. 933-937; (1989).

Benson et al.; "Effects of Natural Eggshell Membrane (NEM) on Cytokine Production in Cultures of Peripheral Blood Mononuclear Cells: Increased Suppression of Tumor Necrosis Factor-Alpha Levels After In Vitro Digestion"; J. Med Food; 14(4); pp. 360-368; (2012).

Gibson et al.; "MMPs Made Easy"; Wounds International; 1(1); pp. 1-6; (2009) available from http://www.woundsinternational.com.

Holmes et al.; "Collagen-Based Wound Dressings for the Treatment of Diabetes-Related Foot Ulcers: a Systematic Review"; Diabetes, Metabolic Syndrome and Obesity: Targets and Therapy; 6; pp. 17-29; (2013).

Kim et al.; "Coaxially Electrospun Micro / Nanofibrous Poly(E-caprolactone) / Eggshell-Protein Scaffold"; Bioninsp. Biomim.; 3; 9 pages; stacks.iop.org/BB/016006; (2008).

Mishra et al.; "Manufacturing Techniques of Orally Dissolving Films"; Pharmaceutical Technology; 35(1); pp. 1-4; (2011).

O'Brien, Fergal J., "Influence of Freezing Rate on Pore Structure in Freeze-dried Collagen-GAG Scaffolds"; Biomaterials; 25(6); pp. 1077-1086; (2004).

O'Brien, Fergal J.; "The Effect of Pore Size on Cell Adhesion in Collagen-GAG Scaffolds"; Biomaterials; 26(4); pp. 433-441; (2005).

Ohto-Fujita et al.; "Hydrolyzed Eggshell Membrane Immobilized on Phosphorylcholine Polymer Supplies Extracellular Matrix Environment for Human Dermal Fibroblasts"; Cell Tissue Res; 345; pp. 177-190; (2011).

(56) References Cited

OTHER PUBLICATIONS

Qin, Yimin; "Review_Aliginate Fibres: An Overview of the Production Processes and Applications in Wound Management"; Polymer International; 57; pp. 171-180; (2008).

Ruff et al.; "Reduction of Pro-Inflammatory Cytokines in Rats Following 7-day Oral Supplementation with a Proprietary Eggshell Membrane-Derived Product"; Modern Research in Inflammation; 3(1); pp. 19-25; (2014).

Cordeiro et al.; "Recent Patents on Eggshell: Shell and Membrane Applications"; Recent Patents on Food, Nutritiion & Agriculture; 3; pp. 1-8; (2011).

Ruff et al.; "Eggshell Membrans: A Possible New Natural Therapeutic for Joint and Connective Tissue Disorders. Results from Two Open-Label Human Clinical Studies"; Clinical Interventions in Aging; 4; pp. 235-240; (2009).

Ruff et al.; "Safety Evaluation of a Natural Eggshell Membrane-Derived Product"; Food and Chemical Toxicology; 50; pp. 604-611; (2012).

Feng Yi et al.; "Soluble Eggshell Mebrane Protein: Antibacterial Property and Biodegradability"; Journal of Wuhan University of Technology-Mater. Sci. Ed.; Sum. 75, vol. 22, No. 1, pp. 117-119; (2007).

Park, J. et al.; "Evaluation of bone healing with eggshell-derived bone graft substitutes in rat calvaria: A pilot study"; Journal of Biomedical Materials Research, vol. 87, Issue No. 1; 2008; pp. 203-214.

Sharma, A. et al.; "Efficacy of supermacroporous poly(ethylene glycol)—gelatin cryogel matrix for soft tissue engineering applications"; Materials Science and Engineering C, vol. 47; 2015; pp. 298-312.

Tan et al.; "A Scanning and Transmission Electron Microscopic Study of the Membranes of Chicken Egg"; Histol Histopath; 7; pp. 339-345; (1992).

World Union of Wound Healing Societies (WUWHS); Principles of Best Practice: Wound Infection in Clinical Practice; An International Consensus; London: MEP Ltd; 12 Pages; (2008) Available from www.mepltd.co.uk.

Yi et al.; "Soluble Eggshell Membrane Protein: Preparation, Characterization and Biocompatibility"; Biomaterials; 25; pp. 4591-4599; (2004).

* cited by examiner

TISSUE ENGINEERING SCAFFOLDS COMPRISING PARTICULATE EGG SHELL MEMBRANE

CROSS REFERENCE TO RELATED APPLICATIONS

This application is a National Stage application of PCT/EP2016/064674 filed on Jun. 24, 2016, which claim the benefit of priority to GB Application Number 1511146.1 filed on Jun. 24, 2015 and GB Application Number 1511579.3 filed on Jul. 1, 2015, all of which are incorporated by reference in their entirety herein.

The present invention provides a three dimensional (3D), porous, biodegradable and biocompatible tissue engineering scaffold comprising particulate egg shell membrane (ESM). More specifically at least 25% w/w of the scaffold is particulate ESM distributed substantially uniformly therein and the scaffold is essentially dry. It has surprisingly been found that such scaffolds perform comparatively to existing scaffolds, both structurally and functionally, but the use of particulate ESM, an abundant by-product of the egg industry composed primarily of structural proteins and extracellular matrix components including collagen, hyaluronic acid, glycosaminoglycans, keratin-like and elastin-like proteins, represents a significantly more cost effective product with reduced pathogen risk and reduced potential for immunological or toxicological problems. The use of such scaffolds in tissue engineering methods, including wound management, bone repair, nerve regeneration, tissue and organ reconstruction and tissue and organ construction are also provided. Such methods may be in vitro or ex vivo as well as in vivo. Simple, cost effective methods for the production of particular scaffolds are also provided.

Both natural and synthetic materials have been used in the art to prepare tissue engineering scaffolds. Such materials are typically polymers capable of forming 3D arrangements and providing suitable and sufficient ligands to promote cell migration, adhesion, proliferation and/or de novo extracellular matrix production. More specific examples include natural (fibrous) proteins and polysaccharides, e.g. those of the extracellular matrix (collagen, fibrin, keratin, elastin and glycosaminoglycans (e.g. hyaluronic acid, chondroitin sulfate, dermatan sulphate, keratan sulphate, heparin, heparan sulphate and hyaluronan)) and alginate, pectin, chitosan, cellulose (including oxidised regenerated cellulose, methylcellulose, carboxymethylcellulose, hydroxyethylcellulose) and fibronectin. Artificial scaffolding materials include PLA (polylactic acid), polyglycolic acid (PGA) and polycaprolactone (PCL), polydioxanone (PDS), poly(ethylene oxide terephthalate) (PEOT) and poly(butylene terephthalate) (PBT), silicon nitride and copolymers thereof, e.g. polylactide-co-glycolide (PLAGA) and PEOT/PBT, hydroxyapatite, and calcium phosphate (Ca—P) and derivatives thereof, e.g. silicated calcium phosphate and beta-tricalcium phosphate (β-TCP).

It is known that 3D protein based structures or matrices assist tissue regeneration in damaged skin and also can promote wound healing in chronic wounds such as ulcers. The paradigm products for commercially available matrices are Integra Dermal Regeneration Template (Integra Biosciences) and Oasis (Healthpoint, Smith & Nephew).

Integra is an open cell sponge manufactured from collagen and glycosaminoglycan and is indicated for full thickness skin repair. It allows cells to migrate through the structure which then promote its resorbtion during the tissue regeneration process. It has space-filling properties and is especially useful in the treatment of burns and chronic wounds. The product is relatively simple in composition and relatively simple to manufacture involving aqueous suspension of collagen and GAG followed by freeze drying to create a dry stable sponge.

Oasis is a layered or lamellar-like structure derived from the porcine small intestine sub-mucosa. It allows cells to attach to the surface and it is resorbed through the wound healing process. It is more topical than space filling although it is replaced by tissue turn-over during the wound healing process. However, it is not an open cell sponge. It is a relatively complex product consisting of decellularized ECM. It is relatively expensive to manufacture.

Recently, it has been shown that intact hen eggshell membrane (ESM) can be used to promote wound healing when placed as an intact film over damaged skin (Yang, J-Y et al. 2003. Chang Gung Med J).

ESM is a complex bi-layered protein-rich fibrous structure found in an avian egg between the albumen and the eggshell. Studies have shown that such membranes contain approximately 90% protein by weight (including collagen, elastin, fibronectin peptide growth factors, ovotrasferrin, lysl oxidase and lysozyme) and desmosine, isodesmosine and glycosaminoglycans (e.g. dermatane sulphate, chondroitin sulphate and hyaluronic acid). These proteins closely reflect the components of the extracellular matrix of vertebrate animals. ESM can readily be separated from the eggshell and the internal components of the egg by a variety of mechanical means to produce an essentially pure preparation of ESM. This procedure is straightforward and low cost giving rise to ample supply of low cost product.

When placed as an intact sheet over a skin wound ESM functions as a semi-permeable membrane and allows moisture vapour transmission and so manages moisture within the wound bed. Its characteristics are similar to synthetic materials such as Biobrane™. However, intact ESM in sizes that are appropriate for use in wound healing contexts is difficult to prepare in commercially viable amounts. Intact ESM requires manual preparation to maintain a useable size and even then it would need to be applied as a mosaic of individual membranes. During processing the delicate material requires separation from residual bound calcium and associated egg white components and either aseptic processing or terminal sterilisation. Process and quality control sufficient for manufacture of a medical product in such contexts are, as a result, not technically or economically feasible.

Powders of ESM of 100-500 μm have also been proposed for the treatment of certain wounds via a topical route of administration (WO 2004/080428). The basis for this proposal is not clear and nor is evidence of successful treatment provided.

Powders of ESM of 100-500 μm have also been proposed for the treatment of pain and inflammation associated with arthritis and other inflammatory conditions via a systemic, in particular oral, route of administration (U.S. Pat. No. 8,580,315).

U.S. Pat. Nos. 3,196,075 and 3,194,732 also describe particles of ESM with dimensions in the micrometre range (fibres and non-fibrous) and their application to wounds as an alternative to a skin graft.

It has now surprisingly been found that particulate ESM can be used to form the basis of cost effective dry tissue engineering scaffolds that perform comparatively to existing dry scaffolds both structurally, e.g. in terms of strength and pliability, and functionally, e.g. as a surface for cellular migration and proliferation and 3D tissue formation. Such scaffolds also have haemostatic properties and wound exudate management capabilities.

Therefore, in a first aspect, the invention provides a three dimensional (3D), porous, biodegradable and biocompatible tissue engineering scaffold, wherein at least about 25% w/w of the scaffold is particulate egg shell membrane (ESM) distributed substantially uniformly therein and the scaffold is essentially dry.

A tissue engineering scaffold may be alternatively described as an artificial structure, more specifically an extracellular matrix, capable of supporting 3D tissue formation following seeding with viable cells and/or implantation into a host organism. The scaffold of the invention may be a dry sponge or foam. The scaffold of the invention is not a gel, in particular a hydrogel or a hydrocolloid gels, nor a woven, non-woven or knitted fibrous sheet structure, e.g. a felt.

A "three dimensional" (3D) object in accordance with the present invention is an object having a height/depth, width and length wherein no one of these dimensions is less than 5%, e.g. less than 10, 15, 20 or 25% of the largest dimension. A 3D object may be described as a space-filling (or void-filling or cavity-filling) entity. These terms should be construed in accordance with the invention as spaces, voids and cavities encountered in tissue engineering contexts. In other words, a 3D structure is not a sheet, film, membrane, layer or coating. In certain embodiments all three dimensions are readily visible to the naked eye, e.g. the shortest dimension will be at least 2 mm, e.g. at least 3, 4, 5, 6, 7, 8, 9 10, 12, 15, 20, 25 or 30 mm.

Biodegradable as used herein refers to the degradation of the scaffold at its site of use, which may be in vivo or in vitro. Typically the scaffold will be designed to have a rate of degradation that is favourable to its intended use. This may be a rate that matches the rate of tissue formation, or at least the formation of extracellular matrix in situ.

Biocompatible as used herein refers to the physiological, e.g. toxicological and/or immunological, tolerability of the scaffold and its degradation products at its site of use and within the host organism. In other words, the ability to be in contact with a living system without producing an adverse effect. ESM and the scaffolds of the invention are predicted to be substantially, e.g. essentially, non-toxic and substantially, e.g. essentially non-immunogenic. Standard assays and acceptable thresholds for biocompatibility, and toxicity in particular, for body-contacting medical devices are provided in the International Standards Authority standard ISO10993 (Biological Evaluation of Medical Devices) and its collateral standards. The scaffolds of the invention are preferably essentially in compliance with ISO10993.

"Porous" as used herein refers to the presence of discrete pores, voids or cells (which terms are used interchangeably) within the scaffold which are permeable to fluids and gases, i.e. at least a portion of the discrete pores are interconnected. The pores of the scaffold may be substantially uniform in size, surface area and/or structure or may be heterogeneous in such metrics. It may be advantageous to control such metrics to optimise the scaffold for its intended use, e.g. by optimising its physical properties (strength, pliability, rate of biodegradation) and/or functional properties (cell proliferation, migration and/or ECM production). This may, for instance, be achieved by controlling production conditions and component materials.

Pore size (or mean or mode pore size if appropriate) may range from 1 µm to 1000 µm, e.g. 1 to 950 µm, 1 to 900 µm, 1 to 850 µm, 1 to 800 µm, 1 to 750 µm, 1 to 700 µm, 1 to 650 µm, 1 to 600 µm, 1 to 550 µm, 1 to 500 µm, 1 to 450 µm, 1 to 400 µm, 1 to 350 µm, 1 to 300 µm, 1 to 250 µm, 1 to 200 µm, 1 to 150 µm, 1 to 100 µm, 1 to 50 µm, 1 to 25 µm, 1 to 10 µm, 2 to 1000 µm, 2 to 950 µm, 2 to 900 µm, 2 to 850 µm, 2 to 800 µm, 2 to 750 µm, 2 to 700 µm, 2 to 650 µm, 2 to 600 µm, 2 to 550 µm, 2 to 500 µm, 2 to 450 µm, 2 to 400 µm, 2 to 350 µm, 2 to 300 µm, 2 to 250 µm, 2 to 200 µm, 2 to 150 µm, 2 to 100 µm, 2 to 50 µm, 2 to 25 µm, 2 to 10 µm, 5 to 1000 µm, 5 to 950 µm, 5 to 900 µm, 5 to 850 µm, 5 to 800 µm, 5 to 750 µm, 5 to 700 µm, 5 to 650 µm, 5 to 600 µm, 5 to 550 µm, 5 to 500 µm, 5 to 450 µm, 5 to 400 µm, 5 to 350 µm, 5 to 300 µm, 5 to 250 µm, 5 to 200 µm, 5 to 150 µm, 5 to 100 µm, 5 to 50 µm, 5 to 25 µm, 5 to 10 µm, 50 µm to 1000 µm, 50 to 950 µm, 50 to 900 µm, 50 to 850 µm, 50 to 800 µm, 50 to 750 µm, 50 to 700 µm, 50 to 650 µm, 50 to 600 µm, 50 to 550 µm, 50 to 500 µm, 50 to 450 µm, 50 to 400 µm, 50 to 350 µm, 50 to 300 µm, 50 to 250 µm, 50 to 200 µm, 50 to 150 µm, 50 to 100 µm, 100 µm to 1000 µm, 100 to 950 µm, 100 to 900 µm, 100 to 850 µm, 100 to 800 µm, 100 to 750 µm, 100 to 700 µm, 100 to 650 µm, 100 to 600 µm, 100 to 550 µm, 100 to 500 µm, 100 to 450 µm, 100 to 400 µm, 100 to 350 µm, 100 to 300 µm, 100 to 250 µm, 100 to 200 µm, 100 to 150 µm, 200 µm to 1000 µm, 200 to 950 µm, 200 to 900 µm, 200 to 850 µm, 200 to 800 µm, 200 to 750 µm, 200 to 700 µm, 200 to 650 µm, 200 to 600 µm, 200 to 550 µm, 200 to 500 µm, 200 to 450 µm, 200 to 400 µm, 200 to 350 µm, 200 to 300 µm, 200 to 250 µm, 300 µm to 1000 µm, 300 to 950 µm, 300 to 900 µm, 300 to 850 µm, 300 to 800 µm, 300 to 750 µm, 300 to 700 µm, 300 to 650 µm, 300 to 600 µm, 300 to 550 µm, 300 to 500 µm, 300 to 450 µm, 300 to 400 µm, 300 to 350 µm, 400 µm to 1000 µm, 400 to 950 µm, 400 to 900 µm, 400 to 850 µm, 400 to 800 µm, 400 to 750 µm, 400 to 700 µm, 400 to 650 µm, 400 to 600 µm, 400 to 550 µm, 400 to 500 µm, 400 to 450 µm, 500 µm to 1000 µm, 500 to 950 µm, 500 to 900 µm, 500 to 850 µm, 500 to 800 µm, 500 to 750 µm, 500 to 700 µm, 500 to 650 µm, 500 to 600 µm, 500 to 550 µm, 600 µm to 1000 µm, 600 to 950 µm, 600 to 900 µm, 600 to 850 µm, 600 to 800 µm, 600 to 750 µm, 600 to 700 µm, 600 to 650 µm, 700 µm to 1000 µm, 700 to 950 µm, 700 to 900 µm, 700 to 850 µm, 700 to 800 µm, 700 to 750 µm, 800 µm to 1000 µm, 800 to 950 µm, 800 to 900 µm, 800 to 850 µm, 900 µm to 1000 µm, or 900 to 950 µm. Any and all ranges derivable from the combination of any of these endpoint values are specifically contemplated.

Different tissue engineering applications may require particular pore sizes and the skilled person would select a pore size that suits his/her particular tissue engineering application. For example, for regeneration of skin using collagen based scaffolds, it has been shown that pore sizes of between 10 µm and 125 µm are optimal (Yannas et al, 1989, PNAS, Vol 86, 933-937). For bone repair, 3D scaffolds have been shown to be functional with pore sizes of 85 µm to 325 µm (Murphy & O'Brien, Cell Adh Migr 4, 377-381; 2010). Other tissues may be optimally regenerated with a different range of pore sizes and the literature on pore size has been recently reviewed by Loh and Choong (Tissue Engineering 19, 485-502; 2013, Table 1 in particular) which is incorporated herein by reference.

The pores of the 3D scaffold of the invention may be substantially uniform in size. For instance, less than 25%, e.g. less than 20%, 15%, 10%, 5% or 1% of the pores in the scaffold will have a size which is outside the selected size range, e.g. those recited above. Expressed alternatively, at least 75%, e.g. 80%, 85%, 90%, 95% or 98% of the pores in the scaffold will have a pore size which differs from the mean or mode pore size by no more than 25%, e.g. by no more than 20%, 15%, 10%, 5% or 1%.

The porosity (or void fraction) of the scaffold, i.e. the proportion of the volume of the scaffold which is void space, may also vary depending on the tissue engineering application to which the scaffold is put to use (Loh and Choong, in particular Table 1 (supra)). In certain embodiments the porosity of the scaffold of the invention may be 30% to 99%, e.g. 30% to 95%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 40% to 99%, 40% to 95%, 40% to 90%, 40% to 85%, 40% to 80%, 40% to 75%, 40% to 70%, 40% to 65%, 40% to 60%, 40% to 55%, 40% to 50%, 40% to 45%, 50% to 99%, 50% to 95%, 50% to 90%, 50% to 85%, 50% to 80%, 50% to 75%, 50% to 50%, 50% to 65%, 50% to 60%, 50% to 55%, 60% to 99%, 60% to 95%, 60% to 90%, 60% to 85%, 60% to 80%, 60% to 75%, 60% to 70%, 60% to 65%, 70% to 99%, 70% to 95%, 70% to 90%, 70% to 85%, 70% to 80%, 70% to 75%, 80% to 99%, 80% to 95%, 80% to 90%, 80% to 85%, 90% to 99%, 90% to 95%, or 95% to 99%. Any and all ranges derivable from the combination of any of these endpoint values are specifically contemplated.

Pore size may be measured by scanning electron microscopy, microcomputed tomography imaging, mercury porosimetry, the permeability-based method or capillary flow porometry. Porosity may be measured by the gravimetric method, mercury porosimetry, the liquid displacement method. These measuring technques are routine and described in detail in Loh and Choong (supra).

The scaffolds of the invention are dry, i.e. are substantially, e.g. essentially, water-free (moisture-free). This may be expressed as a water content of less than 5% w/w, e.g. less than 4.5%, 4%, 3.5%, 3%, 2.5%, 2%, 1.5% or 1% w/w as measured by weight loss on drying or chemically by the Karl Fischer method (United States Pharmacopoeia; European Pharmacopoeia). The scaffolds of the invention are preferably dried by freeze drying (lyophilisation) or by vacuum.

In accordance with the invention the term "particulate ESM" may be a, or may be formed from at least one, particle of ESM having a mean particle diameter of up to 500 µm, e.g. up to 450, 400, 350, 300, 250, 200, 150, 125 or 100 µm. In certain embodiments particulate ESM may be a, or may be formed from at least one, particle of ESM having a mean particle diameter of less than 100 µm, e.g. less than 95, 90, 85, 80, 75, 70, 65, 60, 55, 50, 45, 40, 35, 30, 25, 20, 15, 10, 5, or 1 µm, e.g. less than 900, 850, 800, 750, 700, 650, 600, 550, 500, 450, 400, 350, 300, 250, 200, 150, 100, 50, 10, 5 or 1 nm.

In certain other embodiments particulate ESM may be a, or may be formed from at least one, particle of ESM having a mean particle diameter of equal to or greater than 1 nm, e.g. equal to or greater than 5, 10, 50, 100, 150, 200, 250, 300, 350, 400, 450, 500, 550, 600, 650, 700, 750, 800, 850, 900 or 950 nm, or equal to or greater than 1 µm, e.g. equal to or greater than 5, 10, 15, 20, 25, 30, 35, 40, 45, 50, 55, 60, 65, 70, 75, 80, 85, 90, 95, 100, 125, 150, 200, 250, 300, 350, 400, or 450 µm.

Any and all range endpoints derivable from the combination of any of these values recited above are specifically contemplated.

ESM particles may be any shape. An ESM particle may be essentially symmetric or asymmetric. An ESM particle may be essentially spherical, prismatoidal or cylindrical. An ESM particle may be essentially irregular or regular or have regions of both. An ESM particle may be angular, rounded or tapered or have regions thereof. In certain embodiments an ESM particle may have one length dimension that is significantly greater than the others and so may be referred to as, for example, rod-shaped, needle-shaped or fibrous (rods, needles or fibres) and may be qualified as cylindrical or prismatoidal (e.g. cuboidal) depending on the cross-sectional shape substantially perpendicular to the dimension of significantly greater length.

In certain embodiments an ESM particle may have an aspect ratio between a first length dimension and a second length dimension arranged perpendicular thereto of at least 1.5 (first length dimension:second length dimension), e.g. at least 2, 3, 4, 5, 6, 7, 8, 9, 10, 12, 14, 16, 18, 20, 25, 30, 35, 40, 45, 50, 55, 60, 65, 70, 80, 90 or 100. In other embodiments an ESM particle may have an aspect ratio between a first length dimension and a second length dimension arranged substantially perpendicular thereto of no greater than 2 (first length dimension:second length dimension), e.g. no greater than 3, 4, 5, 6, 7, 8, 9, 10, 12, 14, 16, 18, 20, 25, 30, 35, 40, 45, 50, 55, 60, 65, 70, 80, 90 or 100. Any and all range endpoints derivable from the combination of any of these values are specifically contemplated, e.g. an ESM particle may have an aspect ratio of any of 5, 6, 7, 8, 9 or 10 to any of 20, 25, 30, 35, 40, 45, 50, 55, 60, 65 or 70.

In these embodiments the first length dimension is the longest length dimension in the particle and may be termed the longitudinal dimension. The second length dimension may therefore be termed a lateral dimension. The second length dimension is the longest lateral dimension or a mean average value of the lateral dimensions of the particle.

In certain embodiments the longitudinal dimension is 0.1 µm to 500 µm, e.g. 0.1 µm to 400 µm, 0.1 µm to 300 µm, 0.1 µm to 200 µm, 0.1 µm to 100 µm, 0.1 µm to 80 µm, 0.1 µm to 60 µm, 0.1 µm to 40 µm, 0.1 µm to 20 µm, 0.1 µm to 10 µm, 0.1 µm to 1 µm, 0.1 µm to 0.5 µm, 0.5 µm to 500 µm, 0.5 µm to 400 µm, 0.5 µm to 300 µm, 0.5 µm to 200 µm, 0.5 µm to 100 µm, 0.5 µm to 80 µm, 0.5 µm to 60 µm, 0.5 µm to 40 µm, 0.5 µm to 20 µm, 0.5 µm to 10 µm, 0.5 µm to 1 µm, 1 µm to 500 µm, 1 µm to 400 µm, 1 µm to 300 µm, 1 µm to 200 µm, 1 µm to 100 µm, 1 µm to 80 µm, 1 µm to 60 µm, 1 µm to 40 µm, 1 µm to 20 µm, 1 µm to 10 µm, 10 µm to 500 µm, 10 µm to 400 µm, 10 µm to 300 µm, 10 µm to 200 µm, 10 µm to 100 µm, 10 µm to 80 µm, 10 µm to 60 µm, 10 µm to 40 µm, 10 µm to 20 µm, 20 µm to 500 µm, 20 µm to 400 µm, 20 µm to 300 µm, 20 µm to 200 µm, 20 µm to 100 µm, 20 µm to 80 µm, 20 µm to 60 µm, 20 µm to 40 µm, 40 µm to 500 µm, 40 µm to 400 µm, 40 µm to 300 µm, 40 µm to 200 µm, 40 µm to 100 µm, 40 µm to 80 µm, 40 µm to 60 µm, 60 µm to 500 µm, 60 µm to 400 µm, 60 µm to 300 µm, 60 µm to 200 µm, 60 µm to 100 µm, 60 µm to 80 µm, 80 µm to 500 µm, 80 µm to 400 µm, 80 µm to 300 µm, 80 µm to 200 µm, 80 µm to 100 µm, 100 µm to 500 µm, 100 µm to 400 µm, 100 µm to 300 µm, 100 µm to 200 µm, 200 µm to 500 µm, 200 µm to 400 µm, 200 µm to 300 µm, 300 µm to 500 µm, 300 µm to 400 µm or 400 µm to 500 µm.

In certain embodiments the lateral dimension, or average thereof, is 0.01 µm to 20 µm, e.g. 0.01 µm to 16 µm, 0.01 µm to 12 µm, 0.01 µm to 8 µm, 0.01 µm to 4 µm, 0.01 µm to 2 µm, 0.01 µm to 1.6 µm, 0.01 µm to 1.2 µm, 0.01 µm to 0.8 µm, 0.01 µm to 0.4 µm, 0.01 µm to 0.2 µm, 0.01 µm to 0.1 µm, 0.01 µm to 0.05 µm, 0.05 µm to 20 µm, 0.05 µm to 16 µm, 0.05 µm to 12 µm, 0.05 µm to 8 µm, 0.05 µm to 4 µm, 0.05 µm to 2 µm, 0.05 µm to 1.6 µm, 0.05 µm to 1.2 µm, 0.05 µm to 0.8 µm, 0.05 µm to 0.4 µm, 0.05 µm to 0.2 µm, 0.05 µm to 0.1 µm, 0.1 µm to 20 µm, 0.1 µm to 16 µm, 0.1 µm to 12 µm, 0.1 µm to 8 µm, 0.1 µm to 4 µm, 0.1 µm to 2 µm, 0.1 µm to 1.6 µm, 0.1 µm to 1.2 µm, 0.1 µm to 0.8 µm, 0.1 µm to 0.4 µm, 0.1 µm to 0.2 µm, 0.2 µm to 20 µm, 0.2 µm to 16 µm, 0.2 µm to 12 µm, 0.2 µm to 8 µm, 0.2 µm to 4 µm, 0.2 µm to 2 µm, 0.2 µm to 1.6 µm, 0.2 µm to 1.2 µm, 0.2 µm to 0.8 µm, 0.2 µm to 0.4 µm, 0.4 µm to 20 µm, 0.4 µm to 16 µm, 0.4 µm to 12 µm, 0.4 µm to 8 µm, 0.4 µm to 4 µm, 0.4 µm to 2 µm, 0.4 µm to 1.6 µm, 0.4 µm to 1.2 µm, 0.4 µm to 0.8 µm, 0.8 µm to 20 µm, 0.8 µm to 16 µm, 0.8 µm to 12 µm, 0.8 µm to 8 µm, 0.8 µm to 4 µm, 0.8 µm to 2 µm, 0.8 µm to 1.6 µm, 0.8 µm to 1.2 µm, 1.2 µm to 20 µm, 1.2 µm to 16 µm, 1.2 µm to 12 µm, 1.2 µm to 8 µm, 1.2 µm to 4 µm, 1.2 µm to 2 µm, 1.2 µm to 1.6 µm, 1.6 µm to 20 µm, 1.6 µm to 16 µm, 1.6 µm to 12 µm, 1.6 µm to 8 µm, 1.6 µm to 4 µm, 1.6 µm to 2 µm, 2 µm to 20 µm, 2 µm to 16 µm, 2 µm to 12 µm, 2 µm to 8 µm, 2 µm to 4 µm, 4 µm to 20 µm, 4 µm to 16 µm, 4 µm to 12 µm or 4 µm to 8 µm.

Any and all combinations of longitudinal and lateral dimensions, and ranges thereof, disclosed above are specifically contemplated, in particular in combination with any and all aspect ratios, and ranges thereof. In view of the foregoing it may be seen that certain ESM particles of use in the invention are rods, needles or fibres.

In view of the generality of the invention with regard to ESM particle shape, in the context of ESM particles which are not substantially, e.g. essentially, spherical, references to ESM particle diameters are therefore references to equivalent spherical diameter. In these embodiments the ESM particle has a shape defined by size dimensions that would result in the same size readings as a sphere of the same substance composition of said diameter in the particle size measuring technique used. In certain embodiments the size dimensions used are volume or surface area, preferably volume.

The mean (average) diameter, or equivalent spherical diameter, may be assessed by any convenient means, e.g. resistive pulse/Coulter method, sedimentation (gravity or centrifugation), optical imaging (e.g. SEM, static image analysis, dynamic image analysis), laser diffraction or light scattering, but for the purposes of the invention the Coulter method, in the form of Tunable Resistive Pulse Sensing, or optical means should be used to determine particle size.

It is believed that ESM particles with a high aspect ratio, e.g. fibres, rods or needles, and of the above described sizes (which may be interchangeably referred to herein as microfibres, micro-rods and micro-needles or nano-fibres, nano-rods and nano-needles depending on size) will have certain physical advantages over other forms of ESM (e.g. those of WO 2004/080428) at least in the context of wound healing treatments described herein. In particular, such arrangements are believed to be able to provide ideal levels of surface area, turnover rates, wettability, moisture retention, spreadability and, in particular, MMP inhibition.

The particulate ESM defined above will typically be a plurality of said ESM particles, said plurality of particles having a mode particle diameter up to 500 µm, e.g. up to 450, 400, 350, 300, 250, 200, 150, 125 or 100 µm. In certain embodiments the plurality of particles has a mode particle diameter of less than 100 µm, e.g. less than 95, 90, 85, 80, 75, 70, 65, 60, 55, 50, 45, 40, 35, 30, 25, 20, 15, 10, 5, or 1 µm, e.g. less than 900, 850, 800, 750, 700, 650, 600, 550, 500, 450, 400, 350, 300, 250, 200, 150, 100, 50, 10, 5 or 1 nm.

In certain embodiments the plurality of particles also has a mode particle diameter of equal to or greater than 1 nm, e.g. equal to or greater than 5, 10, 50, 100, 150, 200, 250, 300, 350, 400, 450, 500, 550, 600, 650, 700, 750, 800, 850, 900 or 950 nm, or equal to or greater than 1 µm, e.g. equal to or greater than 5, 10, 15, 20, 25, 30, 35, 40, 45, 50, 55, 60, 65, 70, 75, 80, 85, 90, 95, 100, 125, 150, 200, 250, 300, 350, 400, or 450 µm.

Any and all range endpoints derivable from the combination of any of these values recited above are specifically contemplated.

In certain embodiments less than 25%, e.g. less than 20%, 15%, 10%, 9%, 8%, 7%, 6%, 5%, 4%, 3%, 2%, 1%, 0.5% or 0.1% of the number of particles within said plurality of particles have a mean particle diameter equal to or greater than the mode particle diameter, e.g. a mean particle diameter equal or greater than 500, 450, 400, 350, 300, 250, 200, 150, 125, 100, 95, 90, 85, 80, 75, 70, 65, 60, 55, 50, 45, 40, 35, 30, 25, 20, 15, 10, 5, or 1 µm, e.g. equal to or greater than 900, 850, 800, 750, 700, 650, 600, 550, 500, 450, 400, 350, 300, 250, 200, 150, 100, 50, 10, 5 or 1 nm.

In certain embodiments it may be advantageous to use a plurality of ESM particles with low dispersity. In other embodiments the plurality of ESM particles are essentially monodisperse. On the other hand, in certain other embodiments a broad range of ESM particle sizes or a plurality of more narrow particle size ranges may be selected to achieve one or more of the various physiological effects described herein. Without wishing to be bound by theory, ESM particles of use in the invention having a mean particle diameter at the upper end of the size range may facilitate wound cell migration by providing a greater scaffolding effect whereas ESM particles of use in the invention having a mean particle diameter at the bottom end of the size range may have a greater inhibitory effect on MMPs and inflammation. It may be advantageous to select different size ranges in order to tailor the physiological effects of the ESM particles of use in the invention.

ESM is the fibrous bilayer found in an egg between the albumen and the eggshell of avian eggs, e.g. the eggs of fowl (gamefowl/landfowl (Galliformes) and waterfowl (Anseriformes)) and poultry, in particular chicken, duck, goose, turkey, guineafowl, ostrich, pigeon, pheasant, partridge, grouse or gull. The eggs of *Gallus gallus domesticus*, the domestic chicken, are especially preferred. Either or both layers of the bilayer may be used in accordance with the invention.

Preferably the particulate ESM and the scaffold as a whole is essentially free of other (non-ESM) egg components (which may be considered "contaminating" substances vis a vis ESM), e.g. albumen, yolk, and/or egg shell (calcium carbonate). By "essentially free" it is meant that the particulate ESM (and ESM particles they comprise) of use in accordance with the invention contain no more than 5% w/w, e.g. no more than 4%, 3%, 2%, 1%, 0.5%, 0.1%, 0.05% or 0.01% w/w of non-ESM egg components.

The ESM of the particulate ESM of the invention may be separated from other egg components by any convenient means. The eggs from which the ESM may be separated may be fertilised or unfertilised. The eggs may be intact, i.e. prior to hatching, or may be empty, i.e. the remnants of the egg following hatching or following extraction of the egg contents (albumen and yolk). Suitable means are for example described in WO 2004/080428 and U.S. Pat. No. 8,580,315, the contents of which are incorporated herein by reference. Preferably the ESM is prepared by the method for harvesting eggshell membrane in-line in commercial egg processing plants disclosed in WO 2015/058790 the contents of which are incorporated herein by reference. In brief WO 2015/058790 provides a method of processing eggshell residues, which emanate from an egg breaking unit and comprise eggshell portions as well as membrane portions, comprising feeding eggshell residues (e.g. having a particle size of about 0.5 mm to about 40 mm and a wet basis moisture content of about 3% to about 40%) from the egg breaking unit into a cyclone driven by a process gas having a temperature of less than about 85° C. (preferably of less than about 60° C.) and having a speed exceeding about 60 m/s (preferably between about 70 m/s and about 340 m/s). Within said cyclone vortex processing of the eggshell residues reduces particle size and peels said membrane portions off of said eggshell portions, such that said eggshell portions become separated from said membrane portions. Through a top outlet of said cyclone there is released mainly a mix of process gas, vapour and droplets, and through a bottom outlet of said cyclone there is released mainly a mixture of separated eggshell portions and membrane portions. Said released mixture is then separated into an eggshell portion part and a membrane portion part in a sorting device. The resultant ESM portion may then be processed further into the ESM particles of the invention as described herein, preferably with no intervening steps.

In certain embodiments the method of preparing ESM comprises the further step of controlling time between feeding eggshell residues into and releasing said mixture out of said cyclone by adjusting an eggshell residue feed rate in relation to a total process gas feed rate, e.g. into an interval of about 0.5 s to about 20 s and preferably of about 1 s to about 5 s. In certain embodiments the method further comprises a step of centrifuging the eggshell residues prior to feeding them into said cyclone. In certain embodiments the feeding step is continuous. In other embodiments the sorting step comprises pneumatically expelling the membrane portion part off of sorting screens and out of the sorting device. The method may also comprise a final step of drying the membrane portion part.

ESM material in the form of flakes within the size range of around 1 $mm^2$ to about 10 $mm^2$ cannot be re-formed or processed into a sheet with the same structural characteristics as intact ESM.

In certain embodiments the particulate ESM of use in the invention (or at least the protein components thereof) will be substantially that obtained from the shell-membrane separation process. In other words, the particulate ESM of use in the invention will be substantially chemically unmodified as compared to naturally occurring ESM from a corresponding avian source.

More specifically the particulate ESM of use in the invention will be chemically substantially non-degraded, non-digested (e.g. chemically or enzymatically) and/or non-denatured as compared to naturally occurring ESM from a corresponding avian source. By "substantially non-degraded" it is meant that less than 20%, e.g. less than 15%, 10%, 5% or 1% of the ESM components will show evidence of degradation as compared to naturally occurring ESM from a corresponding avian source. Non-digested and non-denatured should be interpreted accordingly. The degree of degradation/digestion/denaturation of ESM can be assessed by measuring the relative solubility of the ESM and/or the relative size or structure of the collagen fibres in the ESM. This may be achieved through routine techniques including immunohistochemistry/immunocytochemistry techniques and/or biomolecule (e.g. protein) stains and dyes.

In particular in certain embodiments the particulate ESM of use in the invention will not have been exposed to a hydrolysis reaction or a disulphide bond reducing reaction, e.g. chemical or enzymatic, in particular an alkaline hydrolysis reaction. In other words the particulate ESM of use in the invention will be substantially non-hydrolysed, by which it is meant that less than 20%, e.g. less than 15%, 10%, 5% or 1% of the ESM components will show evidence of hydrolysis as compared to naturally occurring ESM from a corresponding avian source. The degree of hydrolysis of ESM can be assessed by measuring the relative solubility of the ESM and/or the relative size of the collagen fibres and/or the extent of collagen cross-linking in the ESM. This may be achieved through routine techniques including immunohistochemistry/immunocytochemistry techniques and/or protein stains and dyes.

In other embodiments the particulate ESM of use in the invention will be substantially, e.g. essentially, insoluble in water at a neutral pH, e.g. pH 6.8-7.2. For the purposes of the invention an insoluble material requires greater than 10 L of solvent to dissolve 1 g of solute.

The particulate ESM of use in the invention may be prepared from ESM by any convenient particle size reduction, micronizing, grinding, pulverizing or milling technology means, e.g. ball milling, bead milling, jet milling, vortex milling, blade milling, rotor-stator dispersement, preferably followed by size selection, e.g. sieving and screening. The chosen particle size reduction method may be either performed dry or with a liquid medium which may or may not comprise other components of the scaffold. Cryo-pulverization may also be employed. In certain embodiments the particle size reduction process, and in certain embodiments the preceding ESM preparation process, is selected on the basis that ESM fibres of the required size (e.g. as recited above) are produced. Inter alia, pulverisation of dry ESM in a blade-mill and rotor-stator dispersement of a suspension of ESM flakes have been shown to be effective in this regard.

Thus, in accordance with the invention, a method for the preparation of particulate ESM of use in the invention may comprise providing ESM, e.g. as defined herein, and subjecting the ESM to a micronization process. Preferably the ESM is provided essentially free of non-ESM egg components and more preferably providing ESM essentially free of non-ESM egg components comprises separating ESM from non-ESM egg components as described in WO 2015/058790 and above and washing the ESM so obtained with a weak acid solution (which term includes a weakly acidic solution), e.g. an aqueous solution of about 0.1% hydrochloric acid or acetic acid, thereby removing any residual calcium carbonate in the ESM. In other embodiments the micronized ESM is washed with said weak acid solution. This weak acid wash, especially treatment with an about 0.1% HCl solution, not only demineralises the ESM, thus minimising the amount of inorganic salts in the ESM, but also removes and/or inactivates infective agents, e.g. microorganisms (e.g. as described herein), prions and viruses.

Micronization of ESM prepared in this way produces ESM fibres of 10-100 µm in length and a thickness of 1-5 µm (i.e. micro-fibres and nano-fibres). Additional components of the scaffold of the invention may be included prior to the micronization process, during said process or after said process. The use of micronized ESM containing particles obtained or obtainable by said methods in the scaffolds of the invention are a further aspect of the invention.

At least about 25% w/w of the scaffold of the invention is particulate egg shell membrane (ESM). The remaining content of the scaffold, i.e. the remaining % w/w up to 100% w/w is provided by further scaffolding materials, essentially inert excipients and/or further therapeutically active agents, preferably further scaffolding materials and/or inert excipients and more preferably further scaffolding materials. In certain embodiments, and as shown in the Examples, the scaffold may consist essentially of particulate ESM.

In certain embodiments the scaffold comprises at least 30% w/w of particulate ESM, e.g. at least 35%, 40%, 45%, 50%, 55%, 60%, 65%, 70%, 75%, 80%, 85%, 90%, 95% w/w or 100% w/w.

In other embodiments the scaffold comprises less than 100% w/w of particulate ESM, e.g. no more than 95% w/w, e.g. no more than 90%, 85%, 80%, 75%, 70%, 65%, 60%, 55%, 50%, 45%, 40%, 35% or 30% w/w.

Any and all range endpoints derivable from the combination of any of these values recited above are specifically contemplated "% w/w" (or "percentage weight by weight") is a commonly used expression of the amount of a compound in a solid. 1% w/w equates to 1 gram of compound per 100 g of solid, 2% w/w equates to 2 g of compound per 100 g of solid, and so on. Accordingly, % w/w may be expressed as g/100 g, grams per 100 grams and g 100 $g^{-1}$. 1% w/w also equates to 10 gram of compound per kilogram of solid. The skilled man would understand that through appropriate scaling calculations, % w/w can be expressed in terms of any SI unit of mass. Conversion into non-standard measures of concentration is also possible and would be routine to the skilled man. When referring to the contents of the scaffold of the invention this is a reference to the dry weight of the scaffold, i.e. in its essentially dry form.

In certain embodiments the scaffold comprises (or consists of, or consists essentially of) particulate ESM and at least one further scaffolding material. In these embodiments it may be advantageous to provide the particulate ESM and the further scaffolding material(s) at a ratio of 1:3 to 20:1, e.g. 1:3 to 15:1, 1:3 to 10:1, 1:3 to 6:1, 1:3 to 5:1, 1:3 to 3:1, 1:3 to 2:1, about 1:1, 1:1 to 20:1, 1:1 to 15:1, 1:1 to 10:1, 1:1 to 6:1, 1:1 to 5:1, 1:1 to 3:1, 1:1 to 2:1, 2:1 to 20:1, 2:1 to 15:1, 2:1 to 10:1, 2:1 to 6:1, 2:1 to 5:1, 2:1 to 3:1, 3:1 to 20:1, 3:1 to 15:1, 3:1 to 10:1, 3:1 to 6:1, 3:1 to 5:1, 5:1 to 20:1, 5:1 to 15:1, 5:1 to 10:1, 5:1 to 6:1, 6:1 to 20:1, 6:1 to 15:1, 6:1 to 10:1, 10:1 to 20:1, 10:1 to 15:1, or 15:1 to 20:1 (ESM:further scaffold material). Any and all ranges derivable from the combination of any of these endpoint values are specifically contemplated.

The exact ratio will be dictated, inter alia, by the particle size of the particulate ESM, the identity of the further scaffolding material(s), the intended use of the scaffold and/or the form of the scaffold. For instance, as shown in the Examples, a sponge scaffold consisting of particulate ESM and collagen may be formed at ESM to collagen ratios of 1:1 and 3:1.

The further scaffolding material may be any suitable scaffolding material other than particulate ESM. In certain embodiments the further scaffolding material will not be sheet or flaked ESM, or indeed solid ESM in any form, or prepared from ESM derived materials or components (e.g. ESM hydrolysates or proteins and/or polysaccharides isolated from ESM). The biodegradable nature of the scaffolds of the invention mean that scaffold does not contain macroscopic metallic components as integral elements.

Suitable scaffolding materials may be natural or synthetic and are typically polymers capable of forming 3D arrangements and providing suitable and sufficient ligands to promote cell migration, adhesion, proliferation and/or de novo extracellular matrix production. More specific examples include natural (fibrous) proteins and polysaccharides, e.g. those of the extracellular matrix (collagen (including all types and forms, preferably collagen I or gelatin), fibrin, keratin, elastin and glycosaminoglycans (e.g. hyaluronic acid, chondroitin sulfate, dermatan sulphate, keratan sulphate, heparin, heparan sulphate and hyaluronan)) and alginate, pectin, chitosan, cellulose (all forms including oxidised regenerated cellulose, methylcellulose, carboxymethylcellulose, hydroxyethylcellulose) and fibronectin. Artificial scaffolding materials include PLA (polylactic acid), polyglycolic acid (PGA) and polycaprolactone (PCL), polydioxanone (PDS), poly(ethylene oxide terephthalate) (PEOT), polyethylene glycol (PEG), polyvinylalcohol (interchangeably referred to as PVA, PVOH or PVAI) and poly(butylene terephthalate) (PBT), silicon nitride and copolymers thereof, e.g. polylactide-co-glycolide (PLAGA) and PEOT/PBT, hydroxyapatite, and calcium phosphate (Ca—P) and derivatives thereof, e.g. silicated calcium phosphate and beta-tricalcium phosphate (β-TCP). Collagen (including all types and forms, preferably collagen I or gelatin) and cellulose (all forms including oxidised regenerated cellulose, methylcellulose, carboxymethylcellulose, hydroxyethylcellulose) are of note. A combination of collagen and oxidised regenerated cellulose may be especially effective as a further scaffolding material. In such embodiments the collagen to oxidised regenerated cellulose ratio will be 70:30 to 30:70, e.g. 65:35 to 35:65, 60:40 to 40:60, 55:45 to 45:55, preferably 55:45. In the context of bone engineering it may be advantageous to incorporate hydroxyapatite, and calcium phosphate (Ca—P) and derivatives thereof, e.g. silicated calcium phosphate and beta-tricalcium phosphate (β-TCP) into the scaffold of the invention, in particular in combination with collagen.

References to alginate include alginic acid unless context dictates otherwise. The alginate may be alginic acid, a divalent metal ion alginate, trivalent metal ion alginate and/or a monovalent metal ion alginate, e.g. those recited above, in particular $Ca^{2+}$ and/or $Na^+$ alginate, respectively. The alginate will typically be a polymer, e.g. of at least 35 kDa, or plurality of polymers of different sizes, although smaller oligomers may be used in place of said polymers or in combination with said polymers. In certain embodiments the further scaffolding material is not alginate and as such the scaffold of the invention does not contain alginate in amounts sufficient to act as a scaffolding material. In certain embodiments the scaffold of the invention does not contain alginate.

The use of collagen and/or gelatin as the sole further scaffolding material(s) is especially preferred. The various ratios recited above apply mutatis mutandis to such embodiments. In certain embodiments the scaffold of the invention consists, or consists essentially, of particulate ESM and collagen and/or gelatin, preferably collagen. In these embodiments the ESM and collagen and/or gelatin are preferably present at ratios of 1:3 to 20:1, e.g. as recited above, preferably about 1:3, about 1:1 or about 3:1, i.e. 25% w/w ESM to 75% w/w collagen and/or gelatin, 50% ESM to 50% collagen and/or gelatin and 75% ESM to 25% collagen and/or gelatin.

The use of PEGs, particularly cross-linked or polymerised PEGs, as the sole further scaffolding material(s) is especially preferred. The various ratios recited above apply mutatis mutandis to such embodiments. In certain embodiments the scaffold of the invention consists, or consists essentially, of particulate ESM and one or more PEGs. In these embodiments the ESM and the PEG are preferably present at ratios of 1:3 to 20:1, e.g. as recited above, preferably about 1:3, about 1:2, about 1:1 or about 3:1, i.e. 25% w/w ESM to 75% w/w PEG, 33% w/w ESM to 67% PEG, 50% ESM to 50% PEG and 75% ESM to 25% PEG. As discussed below, the PEG used may be provided in a non-cross-linked or non-polymerised precursor form and combined with the ESM prior to cross-linking or polymerisation.

The use of polyvinylalcohol (PVA) as the sole further scaffolding materials is especially preferred. The various ratios recited above apply mutatis mutandis to such embodiments. In certain embodiments the scaffold of the invention consists, or consists essentially, of particulate ESM and PVA. In these embodiments the ESM and the PVA are preferably present at ratios of 1:3 to 20:1, e.g. as recited above, preferably about 1:3, about 1:2, about 1:1 or about 3:1, i.e. 25% w/w ESM to 75% w/w PEG, 33% w/w ESM to 67% PEG, 50% ESM to 50% PEG and 75% ESM to 25% PEG.

In certain embodiments the individual molecules of the further scaffolding material may be cross-linked with one another and also, in further embodiments, with the particles of ESM. Any convenient means for cross-linking which are appropriate form the further scaffolding material may be used. Specific examples of crosslinking agents include water soluble carbodiimide crosslinking agents, e.g. 1-Ethyl-3-(3-dimethylaminopropyl)carbodiimide (EDC), and glutaraldehyde, but crosslinking of certain scaffolding materials (e.g. collagen) may be achieved by exposure to certain physical conditions (e.g. the dehydrothermal technique) and/or suitable catalysts (e.g. redox initiators (e.g. ammonium persulfate (APS) or N,N,N,N-tetramethylethylene diamine (TEMED) and photoinitiators (e.g. lithium phenyl(2,4,6-trimethylbenzoyl)phosphinate (LAP)).

Further therapeutically active agents which may be incorporated into the scaffolds of the invention may include, but not be limited to, clinically-useful anti-microbial agents (e.g. antibiotics, antiseptics, antimicrobial surfactants, antifungals, antivirals), a growth factor, or an anti-inflammatory agent (which may be referred to as a "further anti-microbial agent", "further growth factor" or "further anti-inflammatory agent" if the ESM particles used already have such properties). Such agents may be present in the scaffold amounts of less than 25% w/w, e.g. less than 20%, 15%, 10%, 5% or 1% w/w.

Representative antibiotics include, but are not limited to the aminoglycosides (e.g. amikacin, gentamicin, kanamycin, neomycin, netilmicin, streptomycin, tobramycin); the carbecephems (e.g. loracarbef); the 1st generation cephalosporins (eg cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, t roleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the carbapenems (e.g. imipenem, meropenem, ertapenem, doripenem, panipenem/betamipron, biapenem, PZ-601); chloramphenicol; clindamycin, ethambutol; fosfomycin; isoniazid; linezolid; metronidazole; nitrofurantoin; pyrazinamide; quinupristin/ dalfopristin; rifampin; spectinomycin; and vancomycin.

Representative antiseptics include, but are not limited to chlorine bleach (sodium hypochlorite), quaternary ammonium compounds (e.g. benzalkonium chloride, cetyl trimethylammonium bromide, cetylpyridinium chloride), hydrogen peroxide, phenol compounds (e.g. TCP Triclosan), alcohols (e.g. ethanol), Virkon™, iodine compounds (e.g. povidone-iodine), silver, copper, iron, lead, zinc, bismuth, gold and aluminium compounds (e.g. elemental silver, copper, iron, lead, zinc, bismuth, gold and aluminium nano/ microparticles).

Antimicrobial surfactants are another class of antiseptics. These are compounds that disrupt microbial cell membranes and other structural components and therefore inhibit growth and/or viability of microorganisms. Antimicrobial surfactants and their use in antimicrobial compositions is well known in the art should further guidance be needed the discussion of antimicrobial surfactants in "Preservative-free and self-preserving cosmetics and drugs—Principles and practice", Ed. Kabara and Orth, Marcel Dekker, NY, NY, 1997, is explicitly incorporated by reference in its entirety. Antimicrobial surfactants may be anionic, cationic, non-ionic or amphoteric. Examples of antimicrobial anionic surfactants include, but are not limited to, sodium dodecyl sulfate (sodium lauryl sulfate), sodium dodecyl aminopropionic acid, sodium ricinoleate, bile acids, alkylaryl sulfonates, Grillosan DS7911, disodium undecylenic acid monoethanol amidosulfosuccinate. Examples of antimicrobial cationic surfactants include, but are not limited to, the quaternary ammionium compounds, the aminimides and chlorhexidine compounds. Examples of antimicrobial non-ionic surfactants include, but are not limited to, the monoesters of fatty acids, polyethyleneglycomonoesters of alkyldihydroxybenzoic acids, glucosamine derivatives and diethanolamides of N-lauroyl dipeptides. Examples of antimicrobial amphoteric surfactants include, but are not limited to, the alkyl betaines, the alkylamidopropylbetaines, the alkyl aminopropionates, the alkyliminodipropionates and the alkylimidazolines.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type, II interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Representative growth factors include, but are not limited to, platelet-derived growth factor (PDGF), basic and acidic fibroblast growth factor (FGF), epidermal growth factor (EGF), hepatocyte growth factor (hGF), growth hormone (GH), bone morphogenic proteins 2 and 7 (BMP2 and BMP7), insulin-like growth factors I and II (IGF-I, IGF-II), transforming growth factor (TGF-β1, TGF-β2), keratinocyte growth factor (KGF), migration-stimulating factor (MSF), vascular endothelial growth factor (VEGF), nerve growth factor (NGF) and brain-derived neurotrophic factor (BDNF).

Representative anti-inflammatory agents include, but are not limited to an anti-inflammatory steroid (e.g. a corticosteroid), an NSAID or an anti-inflammatory cytokine. Representative NSAIDs include, but are not limited to, the salicylates (e.g. aspirin (acetylsalicylic acid), choline magnesium trisalicylate, diflunisal, salsalate, the propionic acid derivatives (e.g. ibuprofen, dexibuprofen, dexketoprofen, fenoprofen, flurbiprofen, ketoprofen, loxoprofen naproxen, oxaprozin), the acetic acid derivatives (e.g. aceclofenac, diclofenac, etodolac, indomethacin, ketorolac, nabumetone, tolmetin, sulindac), the enolic acid derivatives (e.g. droxicam, isoxicam, lornoxicam, meloxicam, piroxicam, tenoxicam), the anthranilic acid derivatives (e.g. flufenamic acid, meclofenamic acid, mefenamic acid, tolfenamic acid) and the selective COX-2 inhibitors (Coxibs; e.g. celecoxib, etoricoxib, lumiracoxib, parecoxib, rofecoxib, valdecoxib). The propionic acid derivatives (e.g. ibuprofen, dexibuprofen, dexketoprofen, fenoprofen, flurbiprofen, ketoprofen, loxoprofen naproxen, oxaprozin) are preferred, ibuprofen being most preferred. Representative anti-inflammatory cytokines include (IL)-1 receptor antagonist, IL-4, IL-6, IL-10, IL-11, and IL-13.

Examples of suitable excipients are lactose, dextrose, sucrose, sorbitol, mannitol, starches, gum acacia, calcium phosphate, tragacanth, calcium silicate, polyvinylpyrrolidone, propylene glycol, methylhydroxybenzoates, propyl hydroxybenzoates, talc, magnesium stearate, mineral oil or fatty substances such as hard fat or suitable mixtures thereof. The excipients may additionally include lubricating agents, wetting agents, emulsifying agents, suspending agents, preserving agents and the like. In certain embodiments the excipient will not be sheet or flaked ESM, or indeed solid ESM in any form, or prepared from ESM derived materials or components (e.g. ESM hydrolysates or proteins and/or polysaccharides isolated from ESM).

By "distributed uniformly" it is meant that the particulate ESM of the scaffolds of the invention is not accumulated to any significant degree in any part of the scaffold. That is, any sample of a chosen size taken from a scaffold of the invention will have essentially the same amount of particulate ESM (e.g. measured as % w/w) as a second sample of the same size from another part of the scaffold. Expressed differently, a plurality of (e.g. 10) macroscopic portions of a scaffold (e.g. a portion with a volume of about 5 mm$^3$) will on average (mean) contain the essentially the same proportion of particulate ESM as the entire scaffold.

In further embodiments the invention provides a scaffold as defined herein seeded with cells, which may be cells harvested from a target host for the scaffold or those of or derived from a donor. Typical cells for seeding the scaffolds of the invention include stem cells (pluripotent, totipotent, multipotent or unipotent), induced pluripotent stem cells, fibrobalsts, skeletal muscle, smooth muscle, cardiac muscle, epithelial, keratinocyctes, osteoclasts, osteoblasts, basement membrane cells.

In further embodiments the invention provides a scaffold as defined herein adapted for use in wound healing contexts which is covered on one side with a vapour permeable or vapour impermeable barrier to manage moisture within a wound, protect the wound and to provide an anti-microbial barrier.

In further embodiments the invention provides a scaffold as defined herein for use in regeneration and repair of osteochondral defects (cartilage repair) as one of a plurality of scaffold layers of varying gradient pore/fibre structure. This arrangement is preferably designed to mimic the composition and/or structure physiological osteochondral tissue, e.g. the superficial to deep zones of articular cartilage and underlying subchondral bone. For bone repair, the scaffolds have been shown to be functional with pore sizes of 85 µm to 325 µm (Murphy & O'Brien, Cell Adh Migr 4, 377-381; 2010).

The scaffolds of the invention may also be provided as at least one layer of a bi-layered or multi-layered structure optimised for the repair of specific tissue types across anatomical structures. An example is the bi-layered collagen scaffolds described in U.S. Pat. No. 7,780,994 "Composite biomaterials comprising calcium phosphate materials, collagen and glycosaminoglycans". Such scaffolds may be used to bridge articular cartilage and bone, having a predominantly non-calcified porous structure on one side and a predominantly calcified porous structure on the other side. Thus the scaffold is optimized for bone ingrowth on one side and cartilage regeneration on the other.

The scaffolds of the invention may be prepared by any convenient means. To achieve uniform distribution it may be advantageous to combine the particulate ESM with the other scaffold components (if present) prior to formation of the scaffold, e.g. by freeze drying (lyophilisation), cryogelation or evaporation of the mixture. Dependent on the components of the scaffold, the optimum fabrication method may be selected from fused deposition, electrospinning, stereolithography, phase separation, gas forming, selective laser sintering, salt leaching, 3D printing, cryogelation and freeze drying. These methods are routine and are described further by Loh and Choong (supra) and Hwang, H., et al, J. Mater. Chem., 2010, 20, 345-351).

In a specific embodiment there is provided a method for preparing a scaffold of the invention as defined herein in the form of a sponge, said method comprising
  (i) providing particulate ESM, and any other scaffold components if present, in an aqueous suspension in amounts sufficient to yield at least 25% w/w particulate ESM in the scaffold, and
  (ii) freeze drying the suspension, optionally in a mould, thereby obtaining said scaffold.

The any other scaffold components may be suspended and/or dissolved in the particulate ESM suspension.

In certain embodiments step (i) of providing particulate ESM, and any other scaffold components if present, in an aqueous suspension comprises providing ESM in the form of a sheet or flakes, and any other scaffold components if present, in an aqueous suspension, and applying an ESM size reduction technique, e.g. those described herein, to said suspension. The use of a rotor-stator disperser may be advantageous.

In other embodiments step (i) of providing particulate ESM, and any other scaffold components if present, in an aqueous suspension comprises providing particulate ESM and said other scaffold components and combining with an aqueous liquid to form said suspension. This may involve combining one or more of the other scaffold components with an aqueous suspension of said particulate ESM, or combining said particulate ESM with an aqueous solution or suspension of one or more of the other scaffold components, or combining an aqueous suspension of said particulate ESM with an aqueous solution or suspension of one or more of the other scaffold components. Further size reduction may take place at any point.

The mould may be of a size and shape (or approximate shape) appropriate for its intended use, e.g. the size and shape of site to which the scaffold will be applied (e.g. a wound, a joint, a bone defect) or the size and shape of the organ, tissue or portion thereof to which the scaffold will form the basis. In other embodiments the size and shape of the mould is selected to form a product which may be cut to size.

The mould may fully enclose the suspension or at least one face will remain open. By fully enclosing the suspension the expansion of the sponge during freeze-drying may be limited and thereby porosity, pore size and other structural features may be controlled.

In these aspects the other scaffold components may be any of those disclosed herein and the accompanying discussion of preferred features and the like applies mutatis mutandis to these aspects.

In certain embodiments the particulate ESM, and any other scaffold components if present, are provided in an aqueous suspension in amounts sufficient to yield at least 30% w/w of particulate ESM in the scaffold, e.g. at least 35%, 40%, 45%, 50%, 55%, 60%, 65%, 70%, 75%, 80%, 85%, 90%, 95% w/w or 100% w/w.

In other embodiments the particulate ESM, and any other scaffold components if present, are provided in an aqueous suspension in amounts sufficient to yield less than 100% w/w of particulate ESM in the scaffold, e.g. no more than 95% w/w, e.g. no more than 90%, 85%, 80%, 75%, 70%, 65%, 60%, 55%, 50%, 45%, 40%, 35% or 30% w/w.

Any and all range endpoints derivable from the combination of any of these values recited above are specifically contemplated.

In certain embodiments the other scaffold components will comprise, e.g. consist essentially of or consist of collagen and/or gelatin, preferably collagen. In these embodiments the weight ratio of particulate ESM to the collagen and/or gelatin component will be 1:3 to 20:1, e.g. 1:3 to 15:1, 1:3 to 10:1, 1:3 to 6:1, 1:3 to 5:1, 1:3 to 3:1, 1:3 to 2:1 or about 1:1. Further ratios are described herein.

In certain embodiments the other scaffold components will comprise, e.g. consist essentially of or consist of PVA. In these embodiments the weight ratio of particulate ESM to the PVA component will be 1:3 to 20:1, e.g. 1:3 to 15:1, 1:3 to 10:1, 1:3 to 6:1, 1:3 to 5:1, 1:3 to 3:1, 1:3 to 2:1 or about 2:1 or about 1:1. Further ratios are described herein.

In certain embodiments the method includes a step in which the ESM of the particulate ESM provided in step (i) has been or is contacted with an acid at a concentration and for a time sufficient to hydrate the ESM (and preferably solubilise any collagen and/or gelatin present), e.g. acetic acid at a concentration of about 0.5 M (e.g. 0.1 to 1 M, 0.3 to 0.7 M or 0.4 to 0.6 M). Alternative acids may be used but the choice of acid may influence the pore size and mechanical properties of the scaffolds (Ratanavaraporn J et al., J Biomater Sci Polym Ed 19, 945-952; 2008). Acetic acid is preferred for the optimal the preparation of collagen scaffolds.

Freeze drying (lyophilisation) may be achieved by any convenient means and the parameters of which may be adjusted to control the properties of the dry scaffold. By way of example freeze drying may comprise cooling the suspension to about −40° C. at a rate of about 1° C./min, holding at about −40° C. for at least about 1 hour, heating to 0° C. at a rate of about 1° C./min and applying a vacuum of about 200 mTorr (0.266 mbar) for at least about 17 hours.

In another specific embodiment there is provided another method for preparing a scaffold of the invention as defined herein in the form of a sponge, said method comprising (i)(a) providing particulate ESM in an aqueous suspension together with one or more other scaffold components, wherein said other scaffold components are polymerisable or cross-linkable scaffold components, and a suitable initiator of polymerisation or cross-linking in amounts sufficient to yield at least 25% w/w particulate ESM in the scaffold, and (i)(b) maintaining the temperature of the particulate ESM suspension at a temperature below the freezing point of the suspension, optionally in a mould, for a time and under conditions sufficient to allow polymerisation or cross-linking to occur, and (i)(c) drying the polymerised or cross-linked product of step (i)(b) thereby obtaining said scaffold; or (ii)(a) providing particulate ESM in an aqueous suspension together with one or more other scaffold components, wherein said other scaffold components are polymerisable or cross-linkable scaffold components, in amounts sufficient to yield at least 25% w/w particulate ESM in the scaffold, (ii)(b) combining said particulate ESM suspension with a suitable initiator of polymerisation or cross-linking, (ii)(c) maintaining the temperature of the suspension at a temperature below the freezing point of the suspension, optionally in a mould, for a time and under conditions sufficient to allow polymerisation or cross-linking to occur, and (ii)(d) drying the polymerised or cross-linked product of step (ii)(c) thereby obtaining said scaffold; or (iii)(a) providing particulate ESM in an aqueous suspension together with one or more other scaffold components, wherein said other scaffold components are polymerisable or cross-linkable scaffold components, in amounts sufficient to yield at least 25% w/w particulate ESM in the scaffold, (iii)(b) maintaining the temperature of the suspension at a temperature below the freezing point of the suspension, optionally in a mould, (iii)(c) combining said ESM suspension with a suitable initiator of polymerisation or cross-linking for a time and under conditions sufficient to allow polymerisation or cross-linking to occur, and (iii)(d) drying the polymerised or cross-linked product of step (iii)(c) thereby obtaining said scaffold.

The other scaffold components and/or suitable initiator may be suspended and/or dissolved in the suspension of particulate ESM.

In certain embodiments step (i)(a) of providing particulate ESM in an aqueous suspension together with one or more other scaffold components, wherein said other scaffold components are polymerisable or cross-linkable scaffold components, and a suitable initiator of polymerisation or cross-linking comprises providing ESM in the form of a sheet or flakes in an aqueous suspension together with the one or more other scaffold components and the initiator and applying an ESM size reduction technique, e.g. those described herein, to said suspension. The use of a rotor-stator disperser may be advantageous.

In other embodiments step (i)(a) of providing particulate ESM in an aqueous suspension together with the one or more other scaffold components and the initiator comprises providing particulate ESM, said one or more other scaffold components and said initiator, either in their native states or in an aqueous solution or aqueous suspension thereof and combining these forms in any order or simultaneously. This may for instance involve combining one or more of the other scaffold components with an aqueous suspension of said particulate ESM containing the initiator, or combining said particulate ESM with an aqueous solution or suspension of one or more of the other scaffold components and the initiator, or combining an aqueous suspension of said particulate ESM with an aqueous solution or suspension of one or more of the other scaffold components and an aqueous solution or suspension of the initiator. Further size reduction may take place at any point.

In certain embodiments step (ii)(a) and step (iii)(a) of providing particulate ESM in an aqueous suspension together with one or more other scaffold components comprises providing ESM in the form of a sheet or flakes in an aqueous suspension together with the one or more other scaffold components and applying an ESM size reduction technique, e.g. those described herein, to said suspension. The use of a rotor-stator disperser may be advantageous.

In other embodiments step (ii)(a) and step (iii)(a) of providing particulate ESM in an aqueous suspension together with the one or more other scaffold components comprises providing particulate ESM and said one or more other scaffold components and combining with an aqueous liquid to form said suspension. This may involve combining one or more of the other scaffold components with an aqueous suspension of said particulate ESM, or combining said particulate ESM with an aqueous solution or suspension of one or more of the other scaffold components, or combining an aqueous suspension of said particulate ESM with an aqueous solution or suspension of one or more of the other scaffold components. Further size reduction may take place at any point.

The mould may be of a size and shape (or approximate shape) appropriate for its intended use, e.g. the size and shape of site to which the scaffold will be applied (e.g. a wound, a joint, a bone defect) or the size and shape of the organ, tissue or portion thereof to which the scaffold will form the basis. In other embodiments the size and shape of the mould is selected to form a product which may be cut to size.

The mould may fully enclose the suspension or at least one face will remain open. By fully enclosing the suspension the expansion of the sponge during freezing may be limited and thereby porosity, pore size and other structural features may be controlled.

In certain embodiments the particulate ESM is provided in an aqueous suspension in amounts sufficient to yield at least 30% w/w of particulate ESM in the scaffold, e.g. at least 35%, 40%, 45%, 50%, 55%, 60%, 65%, 70%, 75%, 80%, 85%, 90%, 95% w/w or 100% w/w.

In other embodiments the particulate ESM is provided in an aqueous suspension in amounts sufficient to yield less than 100% w/w of particulate ESM in the scaffold, e.g. no more than 95% w/w, e.g. no more than 90%, 85%, 80%, 75%, 70%, 65%, 60%, 55%, 50%, 45%, 40%, 35% or 30% w/w.

Any and all range endpoints derivable from the combination of any of these values recited above are specifically contemplated.

In certain embodiments the other scaffold components will comprise, e.g. consist essentially of, or consist of, a PEG. In these embodiments the weight ratio of particulate ESM to the PEG component will be 1:3 to 20:1, e.g. 1:3 to 15:1, 1:3 to 10:1, 1:3 to 6:1, 1:3 to 5:1, 1:3 to 3:1, 1:3 to 2:1 or about 1:2 or about 1:1. Further ratios are described herein.

As described above in certain embodiments the method includes a step in which the ESM of the particulate ESM provided in step (i)(a), (ii)(a) and/or (iii)(a) has been or is contacted with an acid at a concentration and for a time sufficient to hydrate the ESM A tissue engineering scaffold obtained or obtainable by said methods of the invention is a further aspect of the invention.

The tissue engineering scaffolds of the present invention are predicted to have the capability of acting as scaffolds in any tissue engineering application calling for a biodegradable, biocompatible scaffold.

Thus, the invention provides an in vivo method of tissue engineering, said method comprising providing a tissue engineering scaffold of the invention and applying a sufficient amount of said scaffold to a subject in or on a tissue in need of regeneration, repair or reconstruction or at a site in need of tissue replacement or de novo tissue construction. The scaffold may be seeded with cells capable of forming said tissue prior to application, more preferably the seeded scaffold is cultured under conditions conducive to tissue formation prior to application.

The invention further provides a tissue engineering scaffold of the invention for use in a method of in vivo tissue engineering, e.g. those described herein.

The invention further provides the use of a tissue engineering scaffold of the invention in the manufacture of a medicament for use in a method of in vivo tissue engineering, e.g. those described herein.

In these aspects of the invention the scaffold may be viewed as a pharmaceutical composition (or medicament), comprising at least about 25% w/w of particulate egg shell membrane (ESM), in the form of an essentially dry, three dimensional (3D), porous, biodegradable and biocompatible tissue engineering scaffold in which said particulate ESM is distributed substantially uniformly therein.

The invention also provides an ex vivo method of tissue engineering, said method comprising providing a tissue engineering scaffold of the invention and applying a sufficient amount of said scaffold to a tissue isolated from a subject which is in need of regeneration, repair or reconstruction or at a site in or on said isolated tissue in need of tissue replacement or de novo tissue construction. The scaffold may be seeded with cells capable of forming said tissue prior to application, more preferably the seeded scaffold is cultured under conditions conducive to tissue formation prior to application.

The invention also provides an in vitro method of tissue engineering, said method comprising providing a sufficient amount of said a tissue engineering scaffold of the invention, seeding said scaffold with cells capable of forming said tissue and culturing the scaffold and cells under conditions conducive to tissue formation. The tissue so formed may be implanted in a subject.

The tissue may be selected from adrenal, hepatic, cardiac, renal, pancreatic, pituitary, thyroid, immune, ovarian, testicular, prostate, endometrial, ocular, mammary, adipose, epithelial, endothelial, neural, muscle, connective (e.g. ligament and cartilage), pulmonary, endodermal, epidermal and osseous tissue, preferably muscle, connective (e.g. cartilage), osseous and neural tissue.

References to tissue engineering encompass the engineering of organs, limbs and body parts, or portions or parts or components thereof comprising said tissues, e.g. the adrenal glands, liver, heart, kidneys, pancreas, pituitary gland, thyroid gland, bone marrow, ovaries, testicles, prostate, endometrium, eyes, breast, adipose layers, epithelium, endothelium, nerves, brain, muscle, ligament, cartilage, lung, endodermis, epidermis and bone, preferably the epidermis, muscle, cartilage, bone and nerves.

Thus in certain embodiments the in vivo method of the invention may be a method of epidermal, muscle, bone, cartilage or nerve regeneration, repair, or reconstruction, replacement or de novo generation. In these embodiments the scaffold of the invention will be applied to the organ/tissue in need thereof. In these embodiments the cells to be seeded will be those appropriate to the organ/tissue in need thereof.

Thus in certain other embodiments the in vitro method of the invention may be a method of tissue or organ construction, in particular in vitro methods for constructing epidermis, muscle, bone, cartilage or nerves and organs, limbs and body parts, or portion, parts or components thereof.

The nature of particulate ESM and the scaffolds of the invention carrying said particulate ESM is such that the scaffolds of the invention find particular utility in the management of wounds, especially chronic wounds. The scaffolds of the invention are expected to have haemostatic properties and, when applied dry in particular, wound exudate management capabilities on account of their 3D and porous structure. The scaffold will be also able to provide a space filing effect and act as a support for appropriate tissue growth in the wound whilst inhibiting inappropriate tissue growth, e.g. surgical adhesions, on account of their 3D and porous structure. The chemical and physical properties of particulate ESM also lends functional advantages in the context of wounds, e.g. MMP inhibition, the promotion of cell migration into the wound and/or proliferation or differentiation of wound tissue cells and/or de novo tissue formation, antimicrobial effects and anti-inflammatory effects.

Thus, in certain specific embodiments the invention provides a method to promote the healing of a wound, wherein a tissue engineering scaffold of the invention as defined herein is applied to said wound in an amount sufficient to promote the healing of the wound.

Alternatively, this aspect of the invention provides a tissue engineering scaffold of the invention as defined herein for use in promoting the healing of wounds.

Alternatively still, this aspect of the invention provides the use a tissue engineering scaffold of the invention as defined herein in the manufacture of a medicament for use in promoting the healing of wounds.

Scaffolds seeded with cells from the wounded tissue or cells which promote cell migration into a wound and/or proliferation or differentiation of wound tissue cells and/or de novo tissue formation may be particularly advantageous.

In these aspects of the invention the scaffold may be viewed as a pharmaceutical composition (or medicament), comprising at least about 25% w/w of particulate egg shell membrane (ESM), in the form of an essentially dry, three dimensional (3D), porous, biodegradable and biocompatible tissue engineering scaffold in which said particulate ESM is distributed substantially uniformly therein.

A scaffold of the invention may be used (applied or administered to the wound) on its own (at least initially at the point of contact with the wound) or as part of a composite dressing or scaffold coated implantable medical device. Implantable medical devices include, but are not limited to, any kind of percutaneous devices and/or line which results in a wound (e.g. catheters with cuffs, e.g. Dacron or collagen cuffs), prosthetic devices, e.g., heart valves, artificial joints, and soft tissue implants (e.g. breast, buttock and lip implants), stents and pacemakers. An "implantable" medical device may include a device in which any part of it is contained within the body, i.e. the device may be wholly or partly implanted. In the following, reference to a scaffold of the invention is also a reference to a composite dressing or scaffold coated implantable medical device as described herein, unless context dictates otherwise.

By promotion of wound healing it is meant that the treatment of a wound with a tissue engineering scaffold of the invention as defined herein accelerates the healing process of the wound in question (i.e. the progression of the wound through the three recognised stages of the healing process (i.e. the inflammatory stage, the proliferative stage and/or the remodelling phase)). The acceleration of the healing process may manifest as an increase in the rate of progression through one, two or all of the healing stages. If the wound is a chronic wound that is stalled in one of the healing stages the acceleration might manifest as the restarting of the linear, sequential healing process after the stall. In other words, the treatment shifts the wound from a non-healing state to a state where the wound begins to progress through the healing stages. That progression after the restart may be at a normal rate or even a slower rate compared with the rate a normal acute wound would heal. Promotion of wound healing may also be considered to amount to the prevention of a deceleration the healing process of the wound in question. A deceleration of the healing process may manifest as a decrease in the rate of progression through one, two or all of the healing stages. If the wound is a chronic wound that is restarting on the linear, sequential healing process after a stall deceleration might manifest as a return to being stalled in one of the healing stages. In other words, the treatment prevents a wound from shifting from a healing state to a non-healing state. The promotion of wound healing may further be considered to amount to the treatment of an existing wound or the prevention of the growth of an existing wound and/or an existing healing wound becoming a poorly healing or chronic wound.

In this aspect the treatment of a wound with a tissue engineering scaffold of the invention as defined herein in order to promote healing may reduce the activity of MMPs in a wound against ECM proteins and/or peptide growth or differentiation factors, or least may reduce the overall level of MMP activity or at least may reduce the level of ECM protein and/or peptide growth or differentiation factor degradation. Accordingly the invention can be considered to encompass a method to promote the healing of a wound in which the activity of MMPs in the wound against ECM proteins and/or peptide growth or differentiation factors is reduced or limited, wherein a tissue engineering scaffold of the invention as defined herein is applied to said wound in an amount sufficient to reduce or limit the activity of MMPs in a wound against ECM proteins and/or peptide growth or differentiation factors.

More generally the invention can be considered to encompass a method to promote the healing of a wound in which the overall level of activity of MMPs in the wound is reduced or limited, wherein a tissue engineering scaffold of the invention as defined herein is applied to said wound in an amount sufficient to reduce or limit the overall level of activity of MMPs in a wound.

Also more generally the invention can be considered to encompass a method to promote the healing of a wound in which the degradation of ECM proteins and/or peptide growth or differentiation factors in the wound is reduced or limited, wherein a tissue engineering scaffold of the invention as defined herein is applied to said wound in an amount sufficient to reduce or limit the degradation of ECM proteins and/or peptide growth or differentiation factors in the wound.

MMP-2 (also referred to as 72 kDa type IV collagenase or gelatinase A), MMP-8 (also referred to as neutrophil collagenase or PMNL collagenase) and/or MMP-9 (also referred to as 92 kDa type IV collagenase, 92 kDa gelatinase or gelatinase B) are commonly found in wounds, especially chronic wounds, and in preferred embodiments it is the activity of these MPPs specifically against ECM proteins and/or peptide growth or differentiation factors that is reduced.

In certain embodiments the activity of MMPs in a wound against ECM proteins and/or peptide growth or differentiation factors is reduced or limited to a level that is not detrimental to the healing process of wound undergoing treatment. This reduction may be observed as a reduction in the level of ECM protein (e.g. collagen and elastin) and/or peptide growth or differentiation factor fragments in the wound (or wound fluid), which in turn are an indication of the degradation of these proteins, and which may be detected by routine techniques including immunohistochemistry/immunocytochemistry techniques and/or biomolecule (e.g. protein) stains and dyes or by analysing wound fluid with chromatographic techniques. Limitation may be observed as the maintenance of such levels.

Each wound will require a different (e.g. reduced) level of MMP activity against ECM proteins and/or peptide growth or differentiation factors and even over time the requirements of the same wound in this regard may differ. While this may be determined by the skilled person without undue burden if necessary, a key advantage of the particulate ESM containing tissue engineering scaffolds disclosed herein is that it is relatively easy to achieve an effective level of MMP inhibition and as such onerous dose optimisation is not necessary as routine. Indeed, in most cases any reduction in MMP activity caused by the particulate ESM containing tissue engineering scaffolds defined herein will be effective in promoting wound healing.

Expressed numerically, following application of the scaffold of the invention to the wound undergoing treatment, MMP activity against ECM proteins and/or peptide growth or differentiation factors in a wound (or overall ECM protein and/or peptide growth or differentiation factor degradation) will preferably be reduced by at least 5%, e.g. at least 10%, 15%, 20%, 25%, 30%. In certain embodiments it may be necessary to maintain some level of MMP activity against ECM proteins and/or peptide growth or differentiation factors (or overall ECM protein and/or peptide growth or differentiation factor degradation), and in such embodiments the reduction in MMP activity against ECM proteins and/or peptide growth or differentiation factors (or overall ECM protein and/or peptide growth or differentiation factor degradation) is no more than about 90%, e.g. no more than about 80%, 70%, 60%, 50%, 40%, 30%, 25%, 20%, 15%, 10% or 5%. Any and all range endpoints derivable from the combination of any of these values are specifically contemplated.

Without wishing to be bound by theory, the reduction or limitation in MMP activity against ECM proteins and/or peptide growth or differentiation factors (or overall ECM protein and/or peptide growth or differentiation factor degradation or overall MMP activity) may be on account of a number of mechanisms. This may include, but not be limited to, direct inhibition of the wound MMPs, absorption and deactivation of the wound MMPs, titrating out of the wound MMPs by providing alternative/excess substrate, inhibiting enzymes involved in wound MMP activation (e.g. serine proteases, including plasmin, neutrophil elastase and mast cell chymase), upregulating endogenous inhibitors of MMPs in the wound (e.g. TIMPs; tissue inhibitors of metalloproteinases) inhibiting the expression and/or secretion of MMPs by the cells of the wound and/or inflammatory cells, e.g. monocytes, macrophages, neutrophils and mast cells. The skilled person would be able to measure such effects in a wound without undue burden with routine analytical techniques, some of which are available commercially. The percentage reductions recited above apply in these contexts.

The reduction or limitation in MMP activity against ECM proteins and/or peptide growth or differentiation factors may be reflected in a reduction in or maintenance of overall MMP activity in the wound undergoing treatment. Overall MMP activity is a measure of all MMP activity against all wound substrates. Overall MMP activity can be measured without undue burden with routine analytical techniques, some of which are available commercially. Expressed numerically, following application of the scaffold of the invention to the wound undergoing treatment overall MMP activity in the wound will preferably be reduced by at least about 5%, e.g. at least about 10%, 15%, 20%, 25%, 30%.

In certain embodiments it may be necessary to maintain some level of overall MMP activity, and in particular MMP activity against ECM proteins and/or peptide growth or differentiation factors, and in such embodiments the reduction in overall MMP activity, in particular MMP activity against ECM proteins and/or peptide growth or differentiation factors is no more than about 90%, e.g. no more than about 80%, 70%, 60%, 50%, 40%, 30%, 25%, 20%, 15%, 10% or 5%. Any and all combinations of range endpoints derivable from any of these values are specifically contemplated.

In other embodiments the overall activity of particular MMPs are considered, e.g. MMP-2, MMP-8 and/or MMP-9. In these embodiments overall MMP activity is the activity of the specific MMP in question against all wound substrates.

In one embodiment the method of this aspect of the invention may comprise a step in which the subject will be diagnosed as having a wound that is at risk of inappropriate, i.e. excessive, levels of MMP activity against ECM proteins and/or peptide growth or differentiation factors (or overall levels of MMP activity) or which would benefit from having MMP activity against ECM proteins and/or peptide growth or differentiation factors (or overall levels of MMP activity) reduced or limited (e.g. maintained). In other embodiments the method of this aspect of the invention may comprise a step in which the subject will be diagnosed as having a wound that is at risk of inappropriate, i.e. excessive, levels of ECM protein and/or peptide growth or differentiation factor degradation.

In a further embodiment, the method of this aspect of the invention may comprise, following application of the scaffold of the invention to the wound, a step in which the degradation of ECM proteins and/or peptide growth or differentiation factors is monitored, and/or the MMP activity against ECM proteins and/or peptide growth or differentiation factors is monitored and/or overall MMP activity is monitored. In other embodiments MMPs 2, 8 and/or 9 are considered in place of MMPs in general.

Alternatively or additionally the method of the invention may comprise, following application of the particulate ESM containing tissue engineering scaffolds of the invention to the wound, a step in which a clinical indicator of the wound (for example wound size (depth and/or area), healing time, general discomfort or pain in the wound or surrounding tissue) is monitored. These monitoring steps may involve comparison to the same metric immediately prior to application of the scaffold to the wound or another point even earlier in the subject's treatment.

In this aspect a "sufficient (or effective) amount" of the scaffold of the invention is that amount of scaffold as defined herein which results in the effects on MMP activity and the degradation of ECM proteins and/or peptide growth or differentiation factors effects described above and thereby promotes the healing of the wound. The skilled man would easily be able to determine what an effective (sufficient) amount of the scaffold of the invention would be on the basis of routine dose response protocols and, conveniently, the routine techniques for assessing MMP activity and the degradation of ECM proteins and/or peptide growth or differentiation factors discussed above. In other embodiments a "sufficient (or effective) amount" of the scaffold of the invention is that amount of scaffold as defined herein which results in positive effects on the clinical indicators of the wound described above.

The normal wound healing process involves a proliferation stage in which the cells of the wound tissue migrate into the wound and/or proliferate to form de novo tissue, but in some instances the healing process becomes stuck in a preceding stage.

A wound healing treatment which may promote the viability and/or growth of the cells of the wound tissue would therefore be especially advantageous.

In this aspect the treatment of a wound with a tissue engineering scaffold of the invention as defined herein in order to promote healing may promote the viability and/or growth of the cells of the wound tissue. Accordingly the invention can be considered to encompass a method to promote the healing of a wound in which the viability and/or growth of the cells of the wound tissue is promoted, wherein a tissue engineering scaffold of the invention as defined herein is applied to said wound in an amount sufficient to promote the viability and/or growth of the cells of the wound tissue.

The term "viability and/or growth" should be interpreted consistently with the above discussion in the context of microorganisms (below), although in this instance growth may also include differentiation of the cells of the wound tissue.

By "promoting the growth of the cells of the wound tissue" it is meant that measurable growth (e.g. replication and/or differentiation) of the cells of the wound tissue, or the rate thereof, is increased or at least maintained or prevented from decreasing. Preferably measurable growth (e.g. replication and/or differentiation) of the cells of the wound tissue, or the rate thereof, is increased by at least 5%, more preferably at least 10%, 20%, 30% or 40%, e.g. at least 50%.

In one embodiment the method of this aspect of the invention may comprise a step in which the subject will be diagnosed as having a wound that would benefit from having the viability and/or growth of the cells of the wound tissue promoted.

In a further embodiment, the method of this aspect of the invention may comprise, following application of the scaffold of the invention to the wound, a step in which the viability and/or growth of the cells of the wound tissue, and/or de novo tissue formation, is monitored. These monitoring steps may involve comparison to the same metric immediately prior to application of the scaffold of the invention to the wound or another point even earlier in the subject's treatment.

A wound healing treatment which may promote the migration of the cells of the wound tissue into the wound would therefore also be especially advantageous.

In this aspect the treatment of a wound with a scaffold of the invention as defined herein in order to promote healing may promote the migration of the cells of the wound tissue into the wound. Accordingly the invention can be considered to encompass a method to promote the healing of a wound in which the migration of the cells of the wound tissue into the wound is promoted, wherein a scaffold of the invention as defined herein is applied to said wound in an amount sufficient to promote the migration of the cells of the wound tissue into the wound.

By "promoting migration" it is meant that measurable migration of the cells of the wound tissue into the wound, or the rate thereof, is increased or at least maintained or prevented from decreasing. Preferably measurable migration of the cells of the wound tissue, or the rate thereof, is increased by at least 5%, more preferably at least 10%, 20%, 30% or 40%, e.g. at least 50%.

In one embodiment the method of this aspect of the invention may comprise a step in which the subject will be diagnosed as having a wound that would benefit from having the migration of the cells of the wound tissue into the wound promoted.

In a further embodiment, the method of this aspect of the invention may comprise, following application of the scaffold of the invention to the wound, a step in which the extent of the migration of the cells of the wound tissue into the wound, and/or de novo tissue formation, is monitored. These monitoring steps may involve comparison to the same metric immediately prior to application of the scaffold of the invention to the wound or another point even earlier in the subject's treatment.

The promotion of migration and/or proliferation and/or differentiation may promote de novo tissue formation. The migration of the cells of the wound tissue into the wound, the proliferation and differentiation thereof and de novo tissue formation in the wound may be monitored and quantified by microscopic analysis of the wound or a sample thereof. Such analyses may involve chemical and/or immunochemical staining to detect molecular markers on the cells of the wound tissue and/or de novo tissue in the wound.

In these embodiments the wound cells will be contacted with the scaffold of the invention following application of the scaffold to the wound. More particularly the wound cells will be contacted with an effective amount of the scaffold of the invention effective to promote the viability and/or growth of the cells of the wound tissue, promote the migration of the cells of the wound tissue into the wound or promote de novo tissue formation.

In these embodiments an "effective amount" of the scaffold as defined herein is that amount of the scaffold which results in the pro-proliferation or pro-migration effects described above, or which promotes de novo tissue formation, and thereby further promotes the healing of the wound. The skilled man would easily be able to determine what an effective (sufficient) amount of scaffold would be on the basis of routine dose response protocols and, conveniently, the routine techniques for assessing wound cell viability, growth and migration discussed above.

Wounds are an ideal environment for infection, particularly chronic infection, due to their lack of an epithelial barrier and the availability of substrate and surface for microbial attachment and colonisation. Problematically, infection of a wound often delays healing, by increasing inflammation and necrosis in the wound and surrounding wound tissues, and thus renders that wound more susceptible to established (chronic) infection. Many wounds that struggle to heal comprise an infection and as such a wound healing treatment which may also deal with an infection in the wound (the so called bioburden of the wound) would be especially advantageous.

In this aspect the treatment of a wound with a tissue engineering scaffold of the invention as defined herein in order to promote healing may inhibit the viability and/or growth of a microorganism present in the wound and thereby combat a microbial infection present in the wound. Accordingly the invention can be considered to encompass a method to promote the healing of a wound in which the viability and/or growth of a microorganism present in the wound is inhibited, or in which a microbial infection in the wound is combated, wherein a tissue engineering scaffold of the invention as defined herein is applied to said wound in an amount sufficient to inhibit the viability and/or growth of the microorganism, or to combat the microbial infection.

The term "microorganism" as used herein includes any microbial organism, that is any organism that is microscopic, namely too small to be seen by the naked eye. In particular as used herein the term includes the cellular organisms typically thought of as microorganisms, particularly bacteria, fungi, archaea, algae and protists. The microorganism may be prokaryotic or eukaryotic, and may be from any class, genus or species of microorganism. The microorganism may be aerobic or anaerobic. The microorganism may be pathogenic or non-pathogenic, or may be a spoilage or an indicator microorganism. The microorganism may be drug (i.e. antimicrobial drug, e.g. an antibiotic or an antifungal drug) resistant or multidrug resistant. In particular preferred embodiments the microorganism is capable of colonising a wound and delaying wound healing.

Bacteria or fungi represent preferred classes of microorganism and accordingly the scaffolds of the invention may be preferably viewed as having anti-bacterial or anti-fungal activity (e.g. bactericidal or bacteriostatic or fungicidal or fungistatic).

It is believed that it is not necessary for the scaffolds of the invention to recruit physiological systems or mechanisms (e.g. the immune system) to impart their microbicidal or microbiostatic (e.g. their cytotoxic or cytostatic) effects. Rather, the scaffolds of the invention (or at least the particulate ESM of the scaffolds) act directly on the microorganism.

Preferably the bacteria are selected from the following genera: *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia*.

Thus, the bacteria may be Gram positive or Gram negative bacteria, or indeed Gram-indeterminate bacteria. Gram-negative bacteria are of importance. Within the Gram-negative bacteria the Enterobacteriaceae and the Gram-negative bacteria non-fermenting bacteria are of particular note.

Preferably the bacteria may be selected from the genera *Pseudomonas, Acinetobacter, Burkholderia, Escherichia, Klebsiella, Streptococcus, Enterococcus, Providencia, Moraxalla, Staphylococcus,* e.g. *Pseudomonas aeruginosa, Acinetobacter baumannii, Burkholderia* spp, *E. coli, Klebsiella pneumoniae, Burkholderia cepacia, Burkholderia multivorans, Burkholderia mallei, Burkholderia pseudomallei, Acinetobacter lwoffii, Providencia stuartii, Providencia rettgeri, Providencia alcalifaciens, Klebsiella oxytoca, Pseudomonas anguilliseptica, Pseudomonas oryzihabitans, Pseudomonas plecoglossicida, Pseudomonas luteola, Moraxalla catarrhalis, Enterococcus faecium, Enterococcus faecalis, Streptococcus oralis, Staphylococcus aureus* (e.g. MRSA).

The microorganism may also be a, or from a, fungus, including for example fungi that may be, or may have been, classified as protista, e.g. fungi from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidioides brasiliensis, Blastomyces dermitidis, Pneomocystis carnii, Penicillium marneffi, Alternaria alternate*.

The microorganism may be in a biofilm, or put differently, the microorganism may be in a biofilm mode of growth. By "biofilm" it is meant a community of microorganisms characterized by a predominance of sessile cells that are attached to a substratum or interface or to each other (some motile cells may also be present) and that are embedded in a matrix of extracellular polymers (more specifically extracellular polymers that they have produced) characterised in that the microorganisms of this colony exhibit an altered phenotype with respect to growth rate and gene transcription (for example as compared to their "non-biofilm" or free-floating or planktonic counterparts). By "in a biofilm" it is meant that the microorganism is within (completely or in part), on or associated with the polymer matrix of a biofilm. Viewed differently, microorganisms that are "not in a biofilm" are microorganisms that are either in isolation, e.g. planktonic, or if in an aggregation of a plurality of microorganisms, that aggregation is unorganised and/or is devoid of the matrix characteristic of a biofilm. In each case, the individual microorganisms do not exhibit an altered phenotype that is observed in their biofilm dwelling counterparts.

The term "viability of a microorganism" means the ability of a microbe to survive under given conditions, e.g. in a wound. Survival can be considered equivalent to remaining alive. The scaffolds of the invention may reduce the viability of microorganisms through a microbicidal effect. Determining the viability of a microorganism can be done using the techniques detailed below for measuring microorganism cell death (and viability).

Thus, "inhibiting the viability" of a microorganism can include any effect which reduces the viability of a microorganism, or which renders it less likely to survive, or non-viable. In particular this term covers killing or destroying a microorganism.

The term "killing a microorganism" refers to the act of causing a microorganism to cease to be alive, i.e. to become dead. A microorganism is considered to be alive if it can be induced to replicate and/or grow, or at least display morphological changes, when placed in a medium that would normally support the growth of that microorganism and/or the microorganism is metabolising nutrients to release energy to support cellular functions. Typically, a microorganism can be considered to be dead if cell membrane integrity is lost.

Many routine assays are available to determine if a microorganism is alive (viable) or dead. One option is to place the microorganism in conditions that would normally support the growth of that microorganism and monitor the growth of the microorganism by appropriate standard means, e.g. by monitoring the size of the microorganism, the morphology of the microorganism, the number of microorganisms in the colony over time, the consumption of nutrients in the culture media, etc. Another option is to assess the microorganism for morphologies characteristic of cell death, e.g. necrotic or apoptotic bodies, membrane blebs, nuclear condensation and cleavage of DNA into regularly sized fragments, ruptured cell walls or membranes and leakage of cell contents into the extracellular environment. Other methods exploit the characteristic loss of cell membrane integrity in dead microorganisms. Membrane impermeable dyes (e.g. trypan blue and propidium iodide) are routinely used to assess membrane integrity. A still further option is to measure the metabolism of the microorganism. This can be done routinely in a number of ways. For instance the levels of ATP can be measured.

By "growth of a microorganism" it is meant both an increase in the size of the microorganism or in the amount and/or volume of the constituents of a microorganism (e.g. the amount of nucleic acid, the amount of protein, the number of nuclei, the numbers or size of organelles, the volume of cytoplasm) and an increase in the numbers of a microorganism i.e. an increase in the replication of a microorganism.

By "inhibiting the growth of a microorganism" it is meant that measurable growth (e.g. replication) of a microorganism, or the rate thereof, is reduced. Preferably measurable growth (e.g. replication) of a microorganism, or the rate thereof, is reduced by at least 50%, more preferably at least 60%, 70%, 80% or 90%, e.g. at least 95%. Preferably, measurable growth (e.g. replication) is ceased. Growth in terms of microbial size increase or expansion etc. may be inhibited independently of replication and vice versa. The scaffolds of the invention may inhibit the viability of microorganisms through a microbistatic effect and/or a microbicidal effect.

These aspects of the invention can also be seen to provide an a tissue engineering scaffold of the invention as defined herein for use in combating, and in particular in the treatment of, microbial infection in a wound, or the use of a tissue engineering scaffold of the invention as defined herein in the manufacture of a medicament for use in combating, and in particular in the treatment of, microbial infection in a wound. It will be seen in this aspect that the infection may be combated by inhibiting the growth and/or viability of a microorganism in a subject. The infection may be a biofilm infection.

"Combating an infection" can be viewed as the treatment or prevention of infection, e.g. including the prevention or inhibition of formation of an infection, the reduction or elimination of an infection, a reduction in the number of microbes in the colony making up the infection, a reduction or cessation in the rate of growth of the infection and/or the microorganisms therein, a reduction in or cessation of the rate of expansion in the number of microbes in an infection. "Combating biofilm" includes both preventative and reactionary measures or treatments. Combating biofilm therefore encompasses the prevention or inhibition of formation of a biofilm, the elimination or reduction of a biofilm, a reduction in biofilm size, a reduction in the number of microbes in a biofilm colony, a reduction or cessation in the rate of growth of a biofilm, a reduction in or cessation of the rate of expansion in the number of microbes in a biofilm colony, a reduction in the physical integrity of a biofilm, an increase in the sensitivity of the microbes in a biofilm colony to an anti-microbial agent or host immune defence mechanism and an increase in the permeability of a biofilm to an anti-microbial agent or host immune defence mechanism.

In these embodiments the microorganism will be contacted with the tissue engineering scaffold of the invention as defined herein following application of the scaffold to the wound. The term "contacting" encompasses applying the scaffold directly to a microorganism which is already present in or on the wound, or applying the scaffold to a wound to which the microorganism later comes into contact.

In these embodiments a "sufficient (or effective) amount" of the scaffold of the invention is that amount of scaffold which results in the microbicidal or microbiostatic effects described above, or which effectively combats infection, and thereby promotes the healing of the wound. The skilled man would easily be able to determine what an effective (sufficient) amount of scaffold would be on the basis of routine dose response protocols and, conveniently, the routine techniques for assessing microbial death or growth inhibition etc., as discussed above. The direct effects of the scaffolds of the invention (more particularly the particulate ESM contained therein) can be assessed by using routine in vitro systems familiar to the skilled man which are devoid of complete physiological systems or mechanisms that may interfere with the assessment of microbicidal or microbiostatic effects (e.g. simple cell culture systems, isolated cell/virus systems).

In one embodiment the method of this aspect of the invention may comprise a step in which the subject will be diagnosed as having a wound that is at risk of developing an infection or would benefit from having infection in it treated.

In a further embodiment, the method of this aspect of the invention may comprise, following application of a tissue engineering scaffold of the invention as defined herein to the wound, a step in which the growth and/or viability of a microorganism in the wound or the extent of infection is monitored. These monitoring steps may involve comparison to the same metric immediately prior to application of the scaffold of the invention to the wound or another point even earlier in the subject's treatment.

The normal wound healing process involves an inflammatory stage, but in some instances the healing process becomes stuck in that inflammatory stage and the inflammatory response becomes excessive. As such, a wound healing treatment which may also deal with an excessive inflammatory response in the wound would be especially advantageous.

In this aspect the treatment of a wound with a tissue engineering scaffold of the invention as defined herein in order to promote healing may reduce or limit inflammation in the wound. Accordingly the invention can be considered to encompass a method to promote the healing of a wound in which inflammation in the wound is reduced or limited, wherein a tissue engineering scaffold of the invention as defined herein is applied to said wound in an amount sufficient to reduce or limit inflammation therein.

Inflammation in a wound may be seen as erythema, swelling, local warmth, odema and/or pus. A reduction in the anatomical extent and/or intensity of one or more of these signs of inflammation amounts to a reduction in inflammation. The maintenance of, or prevention of an increase in, the anatomical extent and/or intensity of one or more of these signs of inflammation amounts to a limitation in inflammation.

Alternatively, or in addition, the levels of pro-inflammatory and/or anti-inflammatory markers, e.g. cytokines and chemokines, and/or immune cells in the wound may be measured, e.g. in a sample of wound tissue and/or in a sample from the wound interior. More specifically, the levels of TNFα, IL-1, IL-6, NF-κB, ROS, histamine, macrophages, monocytes, mast cells and/or neutrophils may be measured. This may, for example, be by immunoassay or flow cytometry of a wound sample or a suitable activity assay.

A reduction in the levels of one or more pro-inflammatory markers and/or immune cells in the wound sample may be taken to amount to a reduction in inflammation in the wound. Similarly, an increase in one or more anti-inflammatory markers in a wound sample may be taken to amount to a reduction in the inflammation in a wound. The maintenance of, or prevention of an increase in, the levels of one or more pro-inflammatory markers and/or immune cells or maintenance of, or prevention of a decrease in, the levels of one or more the anti-inflammatory markers in the wound sample may be taken to amount to a limitation of the inflammation in the wound.

In this aspect a "sufficient (or effective) amount" of the scaffold of the invention is that amount of scaffold which results in the effects on the inflammation in a wound described above, in particular the effects on pro- and/or anti-inflammatory marker levels or activities and/or immune cell levels or activities, and thereby further promotes the healing of the wound. The skilled man would easily be able to determine what an effective (sufficient) amount of scaffold would be on the basis of routine dose response protocols and, conveniently, the routine techniques for assessing wound inflammation, as discussed above.

In one embodiment the method of this aspect of the invention may comprise a step in which the subject will be diagnosed as having a wound that is at risk of developing inflammation or would benefit from having inflammation in it treated (i.e. reduced or limited).

In a further embodiment, the method of this aspect of the invention may comprise, following application of the scaffold of the invention to the wound, a step in which the extent of the inflammation in the wound is monitored. These monitoring steps may involve comparison to the same metric immediately prior to application of the scaffold of the invention to the wound or another point even earlier in the subject's treatment.

In certain embodiments the methods of the invention achieve the promotion of wound healing with two or more, or all, of the above described wound effects, e.g. the inhibition of the degradation of ECM and/or peptide growth or differentiation factors (in particular the inhibition of MMP activity against ECM and/or peptide growth or differentiation factors) and one or more of the above described wound effects, in particular the promotion of proliferation, migration and/or differentiation of the cells of the wound tissue and/or de novo tissue formation, but also the antimicrobial effect and/or the anti-inflammatory effects.

In certain embodiments the methods of the invention achieve the promotion of wound healing with either (i) the inhibition of the degradation of ECM and/or peptide growth or differentiation factors (in particular the inhibition of MMP activity against ECM and/or peptide growth or differentiation factors) and one or more, or all, of the above described additional wound effects, in particular the antimicrobial effect and/or the anti-inflammatory effects; or (ii) the reduction in inflammation in the wound and one or more, or all, of the above described additional wound effects, in particular the antimicrobial effect and/or the MMP inhibition effects.

The wound may be found in or on a subject. The term "in a subject" is used broadly herein to include sites or locations inside a subject or on a subject, e.g. an external body surface, and may include in particular a wound containing an implantable a medical device.

Thus, the wound may therefore be found in or on the skin or in or on any susceptible surface in the oral cavity (e.g. gingiva, gingival crevice, periodontal pocket), the reproductive tract (e.g. cervix, uterus, fallopian tubes), the peritoneum, the gastrointestinal tract, the ear, the eye, the prostate, the urinary tract, the vascular system, the respiratory tract, the heart, the kidney, the liver, the pancreas, the nervous system or the brain. The "cells of the wound tissue" should be interpreted accordingly. Preferably the wound is a skin (cutaneous) wound, in other words a dermal or dermatological wound, which includes wounds to any depth of the epidermis and/or dermis and the underlying tissue.

Implantable medical devices include, but are not limited to, any kind of percutaneous devices and/or line which results in a wound (e.g. central venous catheters, in particular catheters with cuffs, e.g. Dacron or collagen cuffs), prosthetic devices, e.g., heart valves, artificial joints, dental implants and soft tissue implants (e.g. breast, buttock and lip implants), stents, pacemakers, and tracheostomy tubes. An "implantable" medical device may include a device in which any part of it is contained within the body, i.e. the device may be wholly or partly implanted.

Wounds may be caused surgically, by physical injury (e.g. mechanical injuries; thermal injuries, for instance those resulting from excessive heat or cold; electrical injuries, for instance those caused by contact with sources of electrical potential; and radiation damage caused, for example, by prolonged, extensive exposure to infrared, ultraviolet or ionizing radiations) or by a spontaneously forming lesion such as a skin ulcer (e.g. a venous, diabetic or pressure ulcer), an anal fissure, a mouth ulcer and acne vulgaris. Surgically grafted tissue is considered to be a wound.

Wounds are typically defined as either acute or chronic. Acute wounds are wounds that proceed orderly through the three recognised stages of the healing process following haemostasis (i.e. the inflammatory stage, the proliferative stage and the remodelling phase) without a protracted timecourse. Chronic wounds are defined as those which fail to heal or where there is excessive skin loss such as through burns. Such wounds do not complete the ordered sequence of biochemical events of the healing process because the wound becomes stalled in one of the healing stages. Commonly, chronic wounds are stalled in the inflammatory phase. Chronic wounds are a major source of morbidity for patients.

In accordance with a particular aspect of the present invention, a chronic wound is a wound that has not healed in the expected amount of time, e.g. healing is taking at least 5, 10, 15, 20 or 30 days longer than expected. This may be taken as a wound which has not healed within at least 30, at least 40 days, particularly at least 50 days, more particularly at least 60 days, most particularly at least 70 days.

Also of particular note are burn wounds. Any burn, in particular a severe burn, has a significant impact on the integrity of the epithelial and/or endothelial barrier of the subject and the healing of such traumas is often a lengthy process. As such, the methods of the invention may be considered to be methods for the promoting the healing of a burn.

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

In certain embodiments the wound is a wound at risk of, or in which there is, an inappropriate, i.e. excessive, level of MMP, e.g. MMP-2, MMP-8 and/or MMP-9, activity against ECM proteins and/or peptide growth or differentiation factors. In other embodiments the wound is a wound at risk of, or in which there is, an inappropriate, i.e. excessive, level of overall MMP activity. In other embodiments the wound is a wound at risk of, or in which there is, an inappropriate, i.e. excessive, level of ECM and/or peptide growth or differentiation factor degradation. Wounds with these features may be identified with the above described methods for measuring ECM protein and/or peptide growth or differentiation factor degradation or for monitoring overall or specific MMP activity against ECM proteins and/or peptide growth or differentiation factors or wound substrates in general.

In certain embodiments the wound is a wound at risk of, or which there is, inappropriate, i.e. insufficient, levels of wound tissue cell migration into the wound and/or proliferation or differentiation of wound tissue cells and/or de novo tissue formation.

In certain embodiments the wound is a wound at risk of, or which contains, a microbial infection, e.g. those disclosed herein. The infection may be acute, or alternatively chronic, e.g. an infection that has persisted for at least 5 or at least 10 days, particularly at least 20 days, more particularly at least 30 days, most particularly at least 40 days.

In certain embodiments the wound is a wound at risk of becoming, or which is, inflamed, e.g. a wound which contains immune cells (e.g. macrophages, monocytes, mast cells and/or neutrophils) and/or inappropriate, i.e. excessive, levels of pro-inflammatory markers (e.g. those disclosed herein) and/or inappropriate, i.e. insufficient, levels of anti-inflammatory markers (e.g. those disclosed herein).

In still further embodiments the wound has two or more, or all, of the above described wound features, e.g. MMP overactivity (in particular against ECM and growth factors) or excessive ECM and growth factor degradation and one or more of the other above described wound features, in particular insufficient levels of wound tissue cell migration into the wound and/or proliferation or differentiation of wound tissue cells and/or de novo tissue formation, but also the antimicrobial effect and/or the anti-inflammatory effects.

In still further embodiments the target wound has either (i) MMP overactivity (in particular against ECM and growth factors) or excessive ECM and growth factor degradation and one or more of the other above described wound features, in particular microbial infection and inflammation; or (ii) excessive inflammation and one or more of the other above described wound features, in particular microbial infection and MMP overactivity (in particular against ECM and growth factors) or excessive ECM and growth factor degradation.

The subject may be any human or non-human animal subject, but more particularly may be a human or non-human vertebrate, e.g. a non-human animal selected from mammals, birds, amphibians, fish and reptiles. Mammalian subjects are preferred. The non-human animal may be a livestock or a domestic animal or an animal of commercial value, including laboratory animals or an animal in a zoo or game park. Representative non-human animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, tilapia, catfish, bream, barramundi, grouper, mullet, amberjack, croaker, rohu, goby, cod, haddock, sea bass and carp. Veterinary uses of the invention are thus covered. The subject may be viewed as a patient. Preferably the subject is a human.

"Treatment" when used in relation to the treatment of a medical condition (e.g. a wound) or infection in a subject in accordance with the invention is used broadly herein to include any therapeutic effect, i.e. any beneficial effect on the condition or in relation to the infection. Thus, not only included is eradication or elimination of the condition/infection, or cure of the subject of the condition/infection, but also an improvement in the infection/condition of the subject. Thus included for example, is an improvement in any symptom or sign of the infection/condition, or in any clinically accepted indicator of the infection/condition (for example a decrease in wound size (depth and/or area), an acceleration of healing time, one or more of the wound effects described herein, or a reduction in general discomfort or pain in the wound or surrounding tissue). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (e.g. an increase in the size of the wound or the development of a chronic or poorly healing wound) or infection or the onset of the condition/infection, or one or more symptoms or indications thereof, for example relative to the condition/infection or symptom or indication prior to the prophylactic treatment. Prophylaxis thus explicitly includes both absolute prevention of occurrence or development of the condition/infection, or symptom or indication thereof, and any delay in the onset or development of the condition/infection or symptom or indication, or reduction or limitation on the development or progression of the condition/infection or symptom or indication.

Specifically, the a tissue engineering scaffold of the invention as defined herein can be used as a prophylactic treatment, for example to prevent, or at least minimise the risk of, wound infection or to prevent, or at least minimise the risk of, an increase in wound size or development of a poorly healing or chronic wound.

The invention will be further described with reference to the following non-limiting Examples in which.

EXAMPLES

Figure 1:
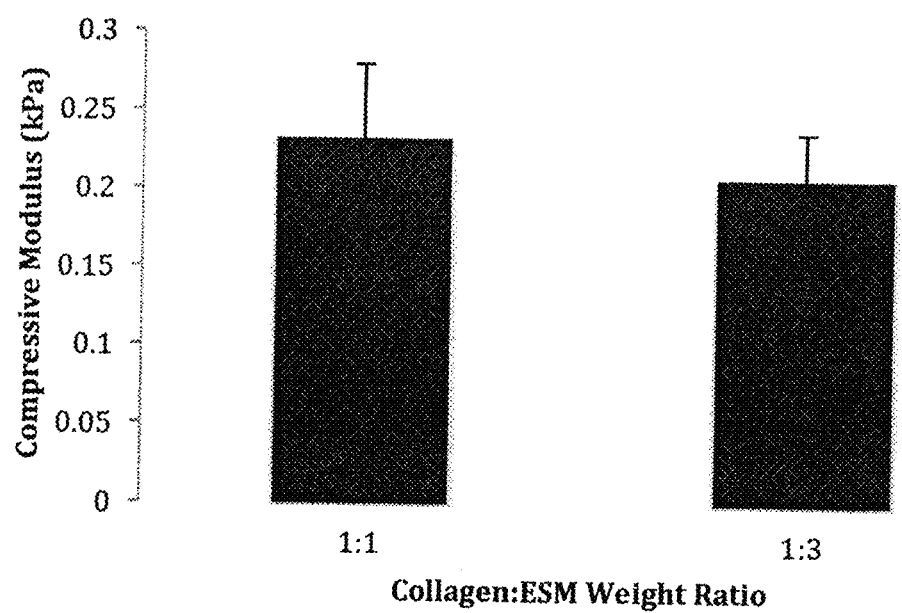
FIG. 1 shows the results of compression tests on collagen: particulate ESM scaffolds of Example 3.

Example 1: Scaffold of 100% w/w Particulate ESM

Raw ESM flakes were purified by acid extraction (0.1 M HCL) and subsequent water washes to restore the pH to approximately neutral. The material was then dried and had the appearance of caked flakes.

The purified ESM material was then suspended in 0.5 M acetic acid at 2% w/v. Acetic acid partially solubilizes collagen and hydrates the ESM which allows a suspension to be more easily created. The mixture was then sheared using a Turrax homogenizer at 14,000 RPM. This shearing resulted in shredding and particle size reduction and created a stable suspension. This was then poured into 12 cm×12 cm trays and freeze dried. During this process, ice crystals form and the ESM is then concentrated and precipitates around the ice droplets. The ice crystals were then sublimed during the drying cycle, resulting in the creation of a stable sponge with open, connected cell structure.

Example 2: Scaffold of 80% w/w Particulate ESM and 20% w/w Collagen

Raw ESM flakes were purified by acid extraction (0.1 M HCL) and subsequent water washes to restore the pH to approximately neutral. The material was then dried and had the appearance of caked flakes.

The purified ESM material was then suspended in a solution of 0.5 M acetic acid at 2% w/v collagen to give a relative solids content of 80% ESM and 20% collagen. The mixture was then sheared using a Turrax homogenizer at 14,000 RPM. The resultant suspension was then poured into 12 cm×12 cm trays and freeze dried, resulting in the creation of a stable sponge of 80% w/w particulate ESM and 20% w/w collagen with open, connected cell structure.

This sponge was more pliable than the pure ESM sponge and may have application where a more flexible sponge may be advantageous, for example in larger wounds with complex surface contours.

Example 3: Scaffolds of Particulate ESM and Collagen and Particulate ESM and Gelatin Scaffolds were produced by freeze-drying collagen and gelatin as carriers for ESM which was added to the protein solutions prior to freeze-drying at various weight ratios (1:1-1:3 Collagen:ESM, 10:3 Gelatin:ESM). Comparison was made between scaffolds which hand been cross-linked using dehydrothermal treatment (105° C., 24 hours) post freeze-drying and those which had not. The resulting cross-linked scaffolds were found to be structurally stable, with a compressive modulus of 206-232 Pa when hydrated. These properties are similar to those of the collagen-based sponge that forms the foundation of Integra's Dermal Regeneration Template.

Preparation of Collagen-Particulate ESM Suspensions:

Eggshell membrane was first ground into fine particles using a blade mill. Collagen suspensions were prepared by adding either 1 or 2 g of collagen to 200 mL of 0.5 M acetic acid (i.e. 0.5 or 1 wt % suspensions). These suspensions were mixed using an overhead blender (Setting 3, Ultra Turrax, IKA Works) for 15 minutes in a cooled (7° C.) reaction vessel. ESM powder (2-12 g, i.e. 0.5-6 wt %) was then added to the suspension and mixed for a further 15 minutes.

Preparation of Gelatin-Particulate ESM Suspensions:

Eggshell membrane was prepared as described previously. Gelatin suspensions were prepared by adding 20 g of gelatin to 200 mL of 0.5 M acetic acid (10 wt % suspension) which was heated to 40° C. on a hot plate and stirred using a magnetic stirrer for 20 min. ESM powder (6 g, 3 wt %) was then added to the suspension and mixed for a further 15 minutes.

Freeze-Drying:

4, 7.5 and 15 mL of collagen-ESM suspension/gelatin-ESM suspension was pipetted into a 61×61 mm stainless steel mould (resulting a scaffold height of approx. 1, 2 and 4 mm). The moulds were then placed in a freeze-dryer (Genesis, VirTis) and frozen by cooling from 20° C. to −40° C. at 1° C./min and holding at this temperature for 1 hour. After this the temperature was increased to 0° C. and a 200 mTorr vacuum (0.266 mbar) was pulled to dry the samples for 17 hours. The shelf was then brought to 20° C. before opening the freeze-drying chamber to prevent condensation of moisture upon the scaffolds.

Dehydrothermal Crosslinking:

Scaffolds were placed in aluminium foil packets and a vacuum was pulled (0.05 bar). The temperature was then increased to 105° C. and held for 24 hours before cooling to room temperature.

Mechanical Testing:

9.5 mm diameter samples were cored from the freeze-dried sheets using a leather punch. These samples were then hydrated for 1 hour in phosphate buffered saline (PBS). Unconfined compression tests were then carried out using a mechanical testing machine (Z050, Zwick/Roell, Germany) fitted with a 5-N load cell. Testing was carried out with impermeable, un-lubricated platens. Tests were conducted at a strain rate of 10%/min. The modulus was defined as the slope of a linear fit to the stress-strain curve over 2-5% strain, avoiding the less stiff toe region of the stress-strain curve.

Cell Migration from Seeded Collagen-ESM Scaffold:

3T3 fibroblast cell line cells (initial cell density: 25,000 cells/cm$^2$, culture medium: DMEM+10% FBS+Pen/Strep) were applied to the top of the collagen-ESM scaffolds and stained with nucleus specific fluorescent probes at day 1 and day 7. A fluorescent microscope (Axiotech microscope; ZEISS) was used to visualise cells on and in the scaffold at these time-points.

Results:

Freeze-drying of the collagen-ESM suspensions resulted in highly uniform scaffolds, with no change in uniformity observed among the range of collagen:ESM weight ratios. The DHT crosslinking treatment improved stability upon hydration in phosphate buffered saline.

Mechanical testing of 4 mm thick samples revealed the compressive moduli of the scaffolds ranged from 232-206 kPa for the 1:1 and 1:3 collagen:ESM weight ratio scaffolds. These values are consistent which the modulus of commercial collagen-based sponges used for wound healing, which have a compressive modulus of approx. 500 kPa. Freeze-drying of the gelatin:ESM suspension resulted in a more brittle scaffold. The pliancy of the gelatin:ESM scaffolds may be modified by change in the manufacturing conditions. Gelatin has an advantage of cost over collagen and may be more suited to more cost sensitive applications.

Cells were detected in and on the scaffold on day 1 and day 7 (data not shown) indicating that cells were persisting in the scaffold and not migrating out of the scaffold.

Example 4: Protocol for EDC Crosslinking

1. Remove the EDC bottle from the freezer and let it sit at room temperature for 30 min to prevent moisture condensation within the bottle. 2. In a sterile culture hood, cut scaffold samples using circular punch (12.7 mm diameter) and place into a 24-well plate with 1 mL PBS in each well to hydrate the scaffolds (place scaffolds in PBS skin-side up). 3. Determine the mass of collagen in the samples. A standard collagen concentration of 1% gives 8 mg for a 12.7 mm diameter scaffold. 4. Calculate and measure the amount of EDC needed to have 6 mmol EDC per gram of collagen/scaffold using the following equation: EDC (g)=weight of collagen (g)×0.006 mol EDC/g collagen×191.7 g EDC/mol EDC 5. Calculate and measure N-Hydroxysuccinimide (NHS) for a 5:2 molar ratio of EDC:NHS. 6. In 50 mL centrifuge tube add 2 mL dd $H_2O$ per scaffold. 7. Add EDC and NHS to the tube and mix with vortex. 8. In a sterile culture hood, use a syringe filter to sterile filter the EDC/NHS solution. 9. Add 2 mL EDC solution to new wells in the 24-well plate. 10. Transfer the scaffolds from the PBS into the EDAC solution and incubate at room temperature for 2 hr. 11. Rinse scaffolds in PBS wells and transfer to an 50 mL tube. 12. Add 25-30 mL of PBS to the container. 13. Incubate for 30 min at room temperature on the orbital shaker at 30 rpm. 14. Replace PBS and repeat rinsing step for another 30 min. 15. Use immediately or store container in the refrigerator (4° C.) for up to 1 week.

Example 5: Protocol for Sterilization and Cell Seeding

1. Place the scaffolds in a 50 mL tube containing 70% ethanol (10-15 scaffolds per tube). Securely place the tubes on an orbital rocker and gently agitate (30 rpm) them for one hour. Change the ethanol in the tubes and repeat this step once. 2. Place the tubes containing the scaffolds into a sterile culture hood and replace the ethanol solution once more. Cap the tubes and gently agitate on an orbital rocker for a further hour. The scaffolds are now sterile and can be hydrated in sterile phosphate buffered saline (PBS). 3. Place the tubes containing the scaffolds into a sterile culture hood and replace the ethanol solution with PBS, cap and agitate for 10 minutes. In order to ensure that the ethanol is fully removed from the hydrogels, wash them in sterile PBS a total of 3 times. 4. Place the scaffolds into sterile 6-well plates (1-3 scaffolds/well). 5. Prepare a $10^7$ cell/mL solution. Seed the top surface of the scaffolds with 100 μL and leave for 20 min. This seeding density is optimised for 12.7 mm diameter samples which are 4 mm thick. 6. Flip the scaffolds and seed what was the bottom surface with 100 μL and leave in the incubator for 20 mins ($2 \times 10^6$ total cells/scaffold). 7. Add 5 mL of media to each well.

Example 6: PVA/ESM Scaffolds—Lyophilization of PVA/ESM Suspensions 75 ml of 10% w/v pharma grade polyvinyl alcohol (PVA) (7.5 g) was mixed with 3.75 g of HCl-washed ESM particles of <100 μm (pH 4.8). This mixture was placed into moulds and freeze dried as described above.

Freeze-drying of PVA/ESM mixtures results in soft pads with enclosed pore structure.

Example 7: PEG/ESM Scaffolds Prepared by Cryogelation

Solutions of 700-polyethyleneglycol-diacrylate (700-PEG-DA), HCl-washed ESM particles of <100 μm (pH 4.8) and the photoinitiator LAP (lithium phenyl(2,4,6-trimethylbenzoyl)phosphinate) in varying concentrations were combined as described in Table 1. Mixtures were frozen in silicon moulds of diverse diameters at −20° C. for 3 to 24 h. After freezing, samples were immediately UV-irradiated at 365 nm for 5 to 15 min at RT, whereupon the methacrylated endgroups of the PEG-DA macromere cross-linked. The ice crystals were allowed to thaw and the cryogels were washed several times with distilled water and dried in vacuum overnight. Results are shown in Table 1

TABLE 1

Different cryogels prepared with varying concentrations of 700-PEG-DA, ESM and LAP.

| 700-PEG-DA [mg/ml $H_2O$] | ESM [mg/ml $H_2O$] | LAP [μg/mg$_{PEG-DA}$] | Cryogel properties |
|---|---|---|---|
| 100 | 0 | 10 | soft, flexible, rubber-like |
| 100 | 100 | 10 | soft, flexible, rubber-like |
| 200 | 0 | 5 | more stable, flexible, rubber-like |
| 200 | 50 | 5 | stable, flexible, rubber-like, ESM particles settle down |
| 200 | 100 | 5 | stable, flexible, rubber-like, homogenous ESM distribution |
| 200 | 100 | 2.5 | stable, flexible, rubber-like, homogenous ESM distribution |
| 300 | 0 | 3.3 | stable, flexible, rubber-like |
| 300 | 50 | 3.3 | stable, flexible, rubber-like, ESM particles settle down |
| 300 | 100 | 3.3 | stable, flexible, rubber-like, homogenous ESM distribution |

Figure 2:
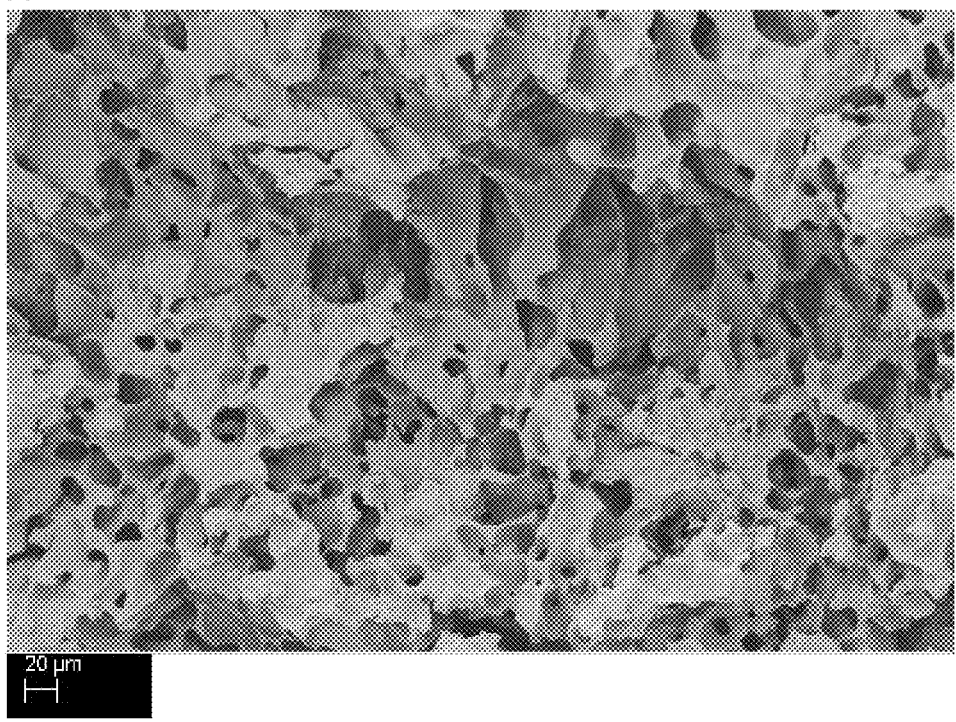
FIG. 2 shows SEM images of a 700-PEG/ESM (30/10) cryogel of Example 7 from the inside (A) and from its surface (B). Interconnected pores between 2 and 20 µm are visable.
Figure 2:
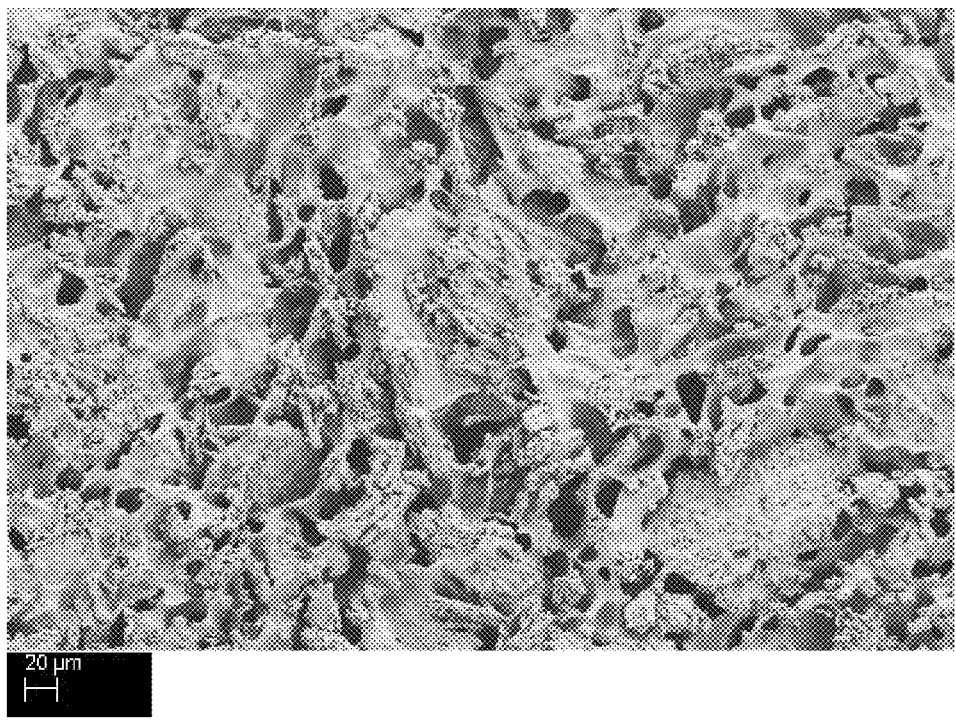

Mixtures of 20 to 30% w/v 700-PEG-DA in water containing 10% w/v ESM (mixtures resulting in scaffolds comprising 33% ESM and 67% PEG w/w or comprising 25% ESM and 75% PEG w/w, respectively) seem to be favourable as deep wound care scaffolds because they are stable, flexible like foam rubber and ESM particles are homogenously distributed within the samples. Lower amounts of particulate ESM in the scaffold results in uneven distribution of the particles in the scaffold. FIG. 2 shows SEM images of a 700-PEG/ESM (30/10) cryogel having interconnected pores between 2 and 20 μm. Since the ESM particle sizes used were in the range of 10 to 100 μm, they sometimes overlap with the cryogel pores.

Cytotoxicity in adherent 3T3 cells caused by the PEG/ESM scaffolds prepared above and free particulate ESM was tested. 3T3 cells (initial cell density: 25,000 cells/cm², culture medium: DMEM+10% FBS+Pen/Strep) were carefully dropped onto the samples. After day 1 and 4, the medium was carefully removed and substituted by the Live/Dead staining solution (30 μg/ml fluorescein diacetate (FDA), 2× GelRed in PBS). Fluorescence staining was captured by Axiotech microscope from ZEISS.

No dead cells were visible in either treatment group (data not shown) showing that the PEG/ESM scaffolds were not cytotoxic to 3T3 cells.

The invention claimed is:

1. A three dimensional (3D), porous, biodegradable and biocompatible tissue engineering scaffold, wherein at least 25% w/w of the scaffold is particulate egg shell membrane (ESM) distributed substantially uniformly therein and the scaffold has a water content of less than 5% w/w.

2. The tissue engineering scaffold of claim 1, wherein said scaffold has a water content of less than 3% w/w.

3. The tissue engineering scaffold of claim 1, wherein said particulate ESM has a mean particle diameter of up to 500 μm.

4. The tissue engineering scaffold of claim 3, wherein said particulate ESM has a mean particle diameter of equal to or greater than 1 nm.

5. The tissue engineering scaffold of claim 1, wherein said particulate ESM is spherical, prismatoidal, cylindrical, rod-shaped, needle-shaped or fibrous.

6. The tissue engineering scaffold of claim 5, wherein said particulate ESM has an aspect ratio between a first length dimension and a second length dimension arranged perpendicular thereto of at least 1.5:1 (first length dimension:second length dimension.

7. The tissue engineering scaffold of claim 1, wherein said scaffold comprises at least 30% w/w of particulate ESM.

8. The tissue engineering scaffold of claim 1, wherein said scaffold comprises at least one further scaffolding material.

9. The tissue engineering scaffold of claim 8, wherein the particulate ESM and the further scaffolding material(s) are present in the scaffold at a ratio of 1–:3 to 20:1 (ESM:further scaffold material).

10. The tissue engineering scaffold of claim 8, wherein said at least one further scaffolding material is selected from the group consisting of collagen, fibrin, keratin, elastin, hyaluronic acid, chondroitin sulfate, dermatan sulphate, keratan sulphate, heparin, heparan sulphate, hyaluronan, alginate, pectin, chitosan, a cellulose, fibronectin, PLA (polylactic acid), polyglycolic acid (PGA), polycaprolactone (PCL), polydioxanone (PDS), poly(ethylene oxide terephthalate) (PEOT), poly(butylene terephthalate) (PBT), polyethylene glycol (PEG), polyvinylalcohol (PVA), silicon nitride, a copolymer of silicon nitride, hydroxyapatite, calcium phosphate (Ca—P), a derivative of Ca—P, and mixtures thereof.

11. The tissue engineering scaffold of claim 10, wherein said at least one further scaffolding material is selected from collagen, gelatin, oxidised regenerated cellulose, methylcellulose, carboxymethylcellulose, hydroxyethylcellulose, polyethylene glycol (PEG), polyvinylalcohol (PVA), hydroxyapatite, silicated calcium phosphate and beta-tricalcium phosphate (β-TCP), and mixtures thereof.

12. The tissue engineering scaffold of claim 8, wherein the individual molecules of the further scaffolding material are cross-linked or polymerised with one another and optionally with the particulate ESM.

13. The tissue engineering scaffold of claim 1, wherein said scaffold does not contain alginate.

14. The tissue engineering scaffold of claim 13, wherein said scaffold comprises at least one further scaffolding material selected from the group consisting of collagen, fibrin, keratin, elastin, hyaluronic acid, chondroitin sulfate, dermatan sulphate, keratan sulphate, heparin, heparan sulphate, hyaluronan, pectin, chitosan, a cellulose, fibronectin, PLA (polylactic acid), polyglycolic acid (PGA), polycaprolactone (PCL), polydioxanone (PDS), poly(ethylene oxide terephthalate) (PEOT), poly(butylene terephthalate) (PBT), polyethylene glycol (PEG), polyvinylalcohol (PVA), silicon nitride, a copolymer of silicon nitride, hydroxyapatite, calcium phosphate (Ca—P), a derivative of Ca—P, and mixtures thereof.

15. The tissue engineering scaffold of claim 1, wherein said scaffold further comprises an antibiotic, an antiviral agent, and antifungal agent, a growth factor, or an anti-inflammatory agent.

16. The tissue engineering scaffold of claim 1, wherein the scaffold is seeded with cells.

17. A method for preparing a scaffold as defined in claim 1 in the form of a sponge, said method comprising
(i) providing particulate ESM, and any other scaffold components if present, in an aqueous suspension in amounts sufficient to yield at least 25% w/w particulate ESM in the scaffold, and
(ii) freeze drying the suspension, optionally in a mold, thereby obtaining said scaffold.

18. A method for preparing a scaffold as defined in claim 1 in the form of a sponge, said method comprising
(i)(a) providing particulate ESM in an aqueous suspension together with one or more other scaffold components, wherein said other scaffold components are polymerisable or cross-linkable scaffold components, and a suitable initiator of polymerisation or cross-linking in amounts sufficient to yield at least 25% w/w particulate ESM in the scaffold, and
(i)(b) maintaining the temperature of the aqueous ESM suspension at a temperature below the freezing point of the suspension, optionally in a mold, for a time and under conditions sufficient to allow polymerisation or cross-linking to occur, and
(i) (c) drying the polymerised or cross-linked product of step (i)(b) thereby obtaining said scaffold; or
(ii) (a) providing particulate ESM in an aqueous suspension together with one or more other scaffold components, wherein said other scaffold components are polymerisable or cross-linkable scaffold components, in amounts sufficient to yield at least 25% w/w particulate ESM in the scaffold,
(ii)(b) combining said aqueous ESM suspension with a suitable initiator of polymerisation or cross-linking,
(ii)(c) maintaining the temperature of the suspension at a temperature below the freezing point of the suspension, optionally in a mold, for a time and under conditions sufficient to allow polymerisation or cross-linking to occur, and
(ii) (d) drying the polymerised or cross-linked product of step (ii)(c) thereby obtaining said scaffold; or
(iii) (a) providing particulate ESM in an aqueous suspension together with one or more other scaffold components, wherein said other scaffold components are polymerisable or cross-linkable scaffold components, in amounts sufficient to yield at least 25% w/w particulate ESM in the scaffold,
(iii)(b) maintaining the temperature of the suspension at a temperature below the freezing point of the suspension, optionally in a mold,
(iii)(c) combining said ESM suspension with a suitable initiator of polymerisation or cross-linking for a time and under conditions sufficient to allow polymerisation or cross-linking to occur, and
(iii)(d) drying the polymerised or cross-linked product of step (iii)(c) thereby obtaining said scaffold.

19. A method of tissue engineering, said method comprising
(i) providing a tissue engineering scaffold as defined in claim 1 and applying a sufficient amount of said scaffold to a subject in or on a tissue in need of regeneration, repair or reconstruction or at a site in need of tissue replacement or de novo tissue construction; or
(ii) providing a tissue engineering scaffold as defined in claim 1 and applying a sufficient amount of said scaffold to an tissue isolated from a subject which is in need of regeneration, repair or reconstruction or at a site in or on said tissue in need of tissue replacement or de novo tissue construction; or
(iii) providing a sufficient amount of the tissue engineering scaffold as defined in claim 1, seeding said scaffold with cells capable of forming said tissue and culturing the scaffold and cells in vitro under conditions conducive to tissue formation.

20. The method of claim 19, wherein said tissue is selected from adrenal, hepatic, cardiac, renal, pancreatic, pituitary, thyroid, immune, ovarian, testicular, prostate, endometrial, ocular, mammary, adipose, epithelial, endothelial, neural, muscle, connective, pulmonary, endodermal, epidermal and osseous tissue, preferably muscle, connective, osseous and neural tissue.

21. A method to promote the healing of a wound, comprising applying a tissue engineering scaffold as defined in claim 1 to said wound in an amount sufficient to promote the healing of the wound.

* * * * *